US012678142B2

(12) United States Patent
Rubin et al.

(10) Patent No.: US 12,678,142 B2
(45) Date of Patent: Jul. 14, 2026

(54) ULTRASOUND SIGNAL CORRELATION PHASE ESTIMATION OF LUNG MOTION

(71) Applicant: THE REGENTS OF THE UNIVERSITY OF MICHIGAN, Ann Arbor, MI (US)

(72) Inventors: Jonathan M. Rubin, Ann Arbor, MI (US); J. Brian Fowlkes, Ann Arbor, MI (US); Oliver D. Kripfgans, Ann Arbor, MI (US); James D. Hamilton, Marina Del Rey, CA (US); Christopher Fung, Ann Arbor, MI (US)

(73) Assignee: REGENTS OF THE UNIVERSITY OF MICHIGAN, Ann Arbor, MI (US)

( * ) Notice: Subject to any disclaimer, the term of this patent is extended or adjusted under 35 U.S.C. 154(b) by 316 days.

(21) Appl. No.: 17/919,162

(22) PCT Filed: May 7, 2021

(86) PCT No.: PCT/US2021/031370
§ 371 (c)(1),
(2) Date: Oct. 14, 2022

(87) PCT Pub. No.: WO2021/226508
PCT Pub. Date: Nov. 11, 2021

(65) Prior Publication Data
US 2023/0165567 A1 Jun. 1, 2023

Related U.S. Application Data

(60) Provisional application No. 63/021,808, filed on May 8, 2020.

(51) Int. Cl.
*A61B 8/00* (2006.01)
*A61B 8/14* (2006.01)
(Continued)

(52) U.S. Cl.
CPC .............. *A61B 8/5223* (2013.01); *A61B 8/14* (2013.01); *G06T 7/12* (2017.01); *G06T 7/246* (2017.01);
(Continued)

(58) Field of Classification Search
None
See application file for complete search history.

(56) References Cited

U.S. PATENT DOCUMENTS

| | | | |
|---|---|---|---|
| 6,381,350 B1 * | 4/2002 | Klingensmith | G06T 7/149 |
| | | | 382/128 |
| 2008/0219405 A1 * | 9/2008 | Falco | A61B 8/4254 |
| | | | 378/65 |

(Continued)

FOREIGN PATENT DOCUMENTS

WO    WO-2019034743 A1    2/2019

OTHER PUBLICATIONS

Chen, X., Zohdy, M. J., Emelianov, S. Y., & O'Donnell, M. (2004). Lateral speckle tracking using synthetic lateral phase. IEEE transactions on ultrasonics, ferroelectrics, and frequency control, 51(5), 540-550. (Year: 2004).*

(Continued)

*Primary Examiner* — Christopher Koharski
*Assistant Examiner* — Renee C Langhals
(74) *Attorney, Agent, or Firm* — MARSHALL, GERSTEIN & BORUN LLP

(57) ABSTRACT

A method of estimating lung motion (e.g., local lung motion and local lung ventilation) includes collecting a time series of ultrasound images of a lung surface, the time series including a plurality of frames, identifying a lung surface in one of the plurality of frames, and subsetting each of the plurality of frames into at least one sub-image. The method further includes applying a high pass temporal filter and a (Continued)

spatial filter. The method still further includes calculating inter-frame motion data from complex data sets associated with one or more pairs of temporally successive frames. In a further method, lung surface longitudinal strain is also calculated.

18 Claims, 19 Drawing Sheets

(51) Int. Cl.
    *G06T 7/12*         (2017.01)
    *G06T 7/246*      (2017.01)

(52) U.S. Cl.
    CPC ............... *G06T 2207/10132* (2013.01); *G06T 2207/30061* (2013.01)

(56)                References Cited

U.S. PATENT DOCUMENTS

| | | | | |
|---|---|---|---|---|
| 2011/0218439 | A1* | 9/2011 | Masui ...................... | A61B 8/08 |
| | | | | 600/443 |
| 2013/0090554 | A1* | 4/2013 | Zvuloni ................. | A61B 5/061 |
| | | | | 600/424 |
| 2013/0197370 | A1* | 8/2013 | Burlina .................. | G06V 10/50 |
| | | | | 600/476 |
| 2018/0360351 | A1 | 12/2018 | Lasenby et al. | |
| 2019/0105013 | A1* | 4/2019 | Wang ..................... | A61B 8/463 |
| 2019/0287248 | A1 | 9/2019 | Abe et al. | |
| 2019/0328346 | A1 | 10/2019 | Kasahara et al. | |

OTHER PUBLICATIONS

Search Report and Written Opinion for International Patent Application No. PCT/US 21/31370, dated Oct. 14, 2021.

* cited by examiner

Lung surface bounds selected. Subsetting images about line 304 300 302

306 302

Sub-image after temporal filtering

306

Sub-image

306

ULTRASOUND SIGNAL CORRELATION PHASE ESTIMATION OF LUNG MOTION

CROSS-REFERENCE TO RELATED APPLICATIONS

This application is a national phase application of International Application No. PCT/US21/31370 filed May 7, 2021, which claims the benefit of U.S. Provisional Application No. 63/021,808 filed May 8, 2020, the entire contents of which are incorporated herein by reference in their entirety.

FIELD OF THE DISCLOSURE

The present disclosure relates generally to techniques for estimating lung motion and, more particularly, to techniques for estimating local lung motion and local lung ventilation using correlation phase determinations.

BACKGROUND

The background description provided herein is for the purpose of generally presenting the context of the disclosure. Work of the presently named inventor, to the extent it is described in this background section, as well as aspects of the description that may not otherwise qualify as prior art at the time of filing, are neither expressly nor impliedly admitted as prior art against the present disclosure.

Respiratory problems can be particularly harmful to patients and can produce lasting deleterious effects. For example, respiratory failure is common with premature births and is a leading cause for the prevalence of ventilatory assistance among infants. For adults, respiratory issues can affect the heart, muscles, and bones. Patients can exhibit shortness of breath, changes to skin, arrhythmias, and loss of consciousness, in some cases.

There are numerous techniques for trying to assess lung performance. These include techniques for assessing inhalation and exhalation motion of the lung, as well as oxygen volumes for each. Commonly, to measure respiratory function, pulmonary function tests are performed, where a patient breathes into a tube and the clinician measures the volume of oxygen during inhalation and exhalation. The techniques are, however, inexact. Other techniques have examined lung surface and measured for strain at the lung surface using speckle tracking as a way of assessing lung condition. Strain is, in some sense, the perfect metric, since strain is positive during inspiration and negative during expiration. However, there are difficulties with the strain metric when applied to humans. One overarching problem in humans is that when the lung moved under ribs, the surface could no longer be tracked. Furthermore, local strain measurements may not work on certain body types, such as people with more subcutaneous fat/tissue, making speckle analysis very difficult.

One metric that is important for ventilator use is positive end-expiratory pressure (PEEP), the positive pressure in the lungs above atmospheric pressure that exists at the end of expiration. Over PEEPing is a major cause of ventilator-induced lung injury. An inability to assess PEEP is one of the major difficulties in ventilator management, and one of the biggest problems faced with ventilator sharing.

Therefore, while there is considerable interest in measuring local lung ventilation, past ultrasound techniques that use speckle tracking to measure strains along the lung surface during respiration are somewhat limiting.

SUMMARY OF THE INVENTION

According to an aspect of the present disclosure, a method of estimating lung motion (e.g., local lung motion and local lung ventilation) incudes collecting a time series of ultrasound images of a lung surface, the time series including a plurality of frames. The method further includes identifying a lung surface in one of the plurality of frames and subsetting, by a processor, each of the plurality of frames into at least one sub-image with the lung surface arranged along the x-axis of the at least one sub-image. The method still further includes applying a spatial filter along an x-axis of each sub-image to transform each pixel of each sub-image into data. The data includes a real component and an imaginary component and is compiled in a complex data set. Each complex data set is associated with one of the plurality of frames. Further, the method includes calculating inter-frame motion data of a window location from the complex data sets associated respectively with a first frame of the plurality of frames and a second frame of the plurality of frames that is temporally successive to the first frame of the plurality of frames.

In some arrangements, identifying a lung surface in one of the plurality of frames may include drawing a line between a right edge and a left edge of the lung surface in one of the plurality of frames. The line may be drawn by an operator using software on a computer. Subsetting each of the plurality of frames into at least one sub-image may be based on a location of the line. Subsetting each of the plurality of frames of the time series may include, for the one of the plurality of frames on which the line is drawn, identifying a sub-image having a fixed number of pixels above the line and below the line, and for remaining frames of the plurality of frames, identifying a sub-image for each of the remaining frames having a same set of pixels as the sub-image of the one of the plurality of frames on which the line is drawn. In other arrangements, identifying a lung surface in one of the plurality of frames and subsetting each of the plurality of frames into at least one sub-image is automated by use of image segmentation algorithms.

In some arrangements, the spatial filter is a synthetic phase filter or a gradient filter. Other arrangements may include applying a spatial filter along a y-axis of each sub-image.

In some arrangements, the data may be pulse-range data represented by $s(x)=A(x-U)e^{-i2\pi f(x-U)}$, where x is a pixel, U is a position of a signal, $A(x-U)$ is a signal amplitude profile, and f is a spatial center frequency of a complex signal. Calculating inter-frame motion data may include extracting a first signal from a correlation window of the first frame and a second signal from the correlation window of the second frame, the correlation window being a same location in the first frame and the second frame, where the first signal is represented by $s_1(x)=A_1(x-U_1)e^{-i2\pi f(x-U_1)}$ and the second signal is represented by $s_2(x)=A_2(x-U_2)e^{-i2\pi f(x-U_2)}$. Further, calculating inter-frame motion data may include calculating a sum of a complex conjugate multiple of the first signal and the second signal, which is a zero lag covariance of $s_1$ and $s_2$ and is represented by $$\sigma(0) = \sum_x s_2(x) * s_1^*(x) = \sum_x A_2(x-U_2)e^{-i2\pi f(x-U_2)}A_1(x-U_1)e^{i2\pi f(x-U_1)}.$$

Calculating inter-frame motion data may still further comprise calculating a phase angle of the zero lag covariance of $s_1$ and $s_2$, which is represented by angle $$(\sigma(0)) = \text{angle } (s_2(x) * s_1^*(x)) = 2\pi f(U_2 - U_1),$$

and calculating a lag 1 covariance represented by $$\sigma(1) = \sum_x s_2(x-1) * s_1^*(x) =$$
$$\sum_x A_2(x-1-U_2)e^{-i2\pi f(x-U_2-1)}A_1(x-U_1)e^{i2\pi f(x-U_1)}.$$

Calculating inter-frame motion data may still further include calculating a phase angle of a complex conjugate multiple of the zero lag covariance and the lag 1 covariance as represented by angle($\sigma(1)\sigma^*(0)$)=$2\pi$. Calculating inter-frame motion data further may include calculating a displacement represented by $\Delta U_{1,2}=2\pi f(U_2-U_1)/2\pi f$.

In still further arrangements, the method may include identifying pairs of the plurality of frames, each frame having a temporally successive frame and identified as forming a pair that includes the frame and the temporally successive frame, and calculating inter-frame motion for all pairs of the plurality of frames from the complex data sets associated with the frame and the temporally successive frame of each pair. The displacement may be calculated for each window location of each sub-image for all pairs of the plurality of frames. The displacement for each window location may be assigned to the center pixel of the window location. A segmentation algorithm may be applied to identify pixels from the lung surface, and lung surface motion may be calculated from the displacement of pixels identified as the lung surface.

In some arrangements, the method may include applying a high pass temporal filter, a band pass filter, or an all pass filter to each sub-image.

In some arrangements, the method may further include calculating a lung surface longitudinal strain by dividing each frame of the plurality of frames into a right segment and a left segment, calculating a mean displacement for the right segment, calculating a mean displacement for the left segment, finding a difference between the mean displacement for the right segment and the mean displacement for the left segment, and dividing the difference by a distance between a center position of the right segment and a center position of the left segment to determine instantaneous strain. The method may further include determining instantaneous strain for all frames of the plurality of frames, identifying a maximum instantaneous strain determined for any of the frames of the plurality of frames, identifying a minimum instantaneous strain determined for any of the frames of the plurality of frames, and subtracting the minimum instantaneous strain from the maximum instantaneous strain to determine a strain change over the plurality of frames.

According to an aspect of the present disclosure, a method of estimating lung motion, the method includes collecting a time series of ultrasound images of a lung surface, the time series including a plurality of frames. The method further includes identifying a lung surface in one of the plurality of frames. The method further includes subsetting, by a processor, each of the plurality of frames into at least one sub-image to form a raw set of sub-images. The method further includes applying a tissue region mask to each sub-image in the raw set of sub-images to create a tissue region mask set of sub-images. The method further includes applying a temporal filter within a robustness stage to each sub-image in the raw set of sub-images to create a temporally filtered robustness set of sub-images. The method further includes applying a lung surface mask to each sub-image in the raw set of sub-images to create a lung surface mask set of sub-images. The method further includes applying a temporal filter within a precision stage to each sub-image in the raw set of sub-images to create a temporally filtered precision set of sub-images. The method further includes performing tissue tracking by tracking the raw set of sub-images and the tissue region mask set of sub-images to create tissue tracking data. The method further includes performing lung tracking by tracking the temporally-filtered robustness set of sub-images and the lung surface mask set of sub-images to create first lung tracking data, tracking the temporally filtered precision set of sub-images and the lung surface mask set of sub-images to create second lung tracking data, and combining the first lung tracking data and the second lung tracking data to create stage combination data. The method further includes quantifying displacement and strain based on the tissue tracking data and the stage combination data.

In some arrangements, tracking the raw set of sub-images and the tissue region mask set of sub-images to create tissue tracking data may include selecting an image down sampling factor comprising a plurality of down sample values, selecting a track direction, and for each down sample value, calculating displacement, strain, and correlation in the track direction from the raw set of sub-images and the tissue region mask set of sub-images.

In some arrangements tracking the temporally-filtered robustness set of sub-images and the lung surface mask set of sub-images to create first lung tracking data may include iteratively selecting an image down sampling factor comprising a plurality of down sample values, selecting a track direction, and for each down sample value, calculating displacement, strain, and correlation in the track direction from the temporally-filtered robustness set of sub-images and the lung surface mask set of sub-images, wherein, after an initial iteration, calculating displacement and strain includes utilizing a previously calculated displacement, strain, or correlation associated with one of the plurality of down sample values.

In some arrangements, tracking the temporally filtered precision set of sub-images and the lung surface mask set of sub-images to create second lung tracking data may include iteratively selecting an image down sampling factor comprising a plurality of down sample values, selecting a track direction, and for each down sample value, calculating displacement, strain, and correlation in the track direction from the temporally-filtered precision set of sub-images and the lung surface mask set of sub-images, wherein, after an initial iteration, calculating displacement and strain includes utilizing a previously calculated displacement, strain, or correlation associated with one of the plurality of down sample values.

In some arrangements combining the first lung tracking data and the second lung tracking data to create stage combination data may include providing a displacement, strain, and correlation set forming the first lung tracking data, the displacement, strain, and correlation set forming the first lung tracking data including a displacement value, a strain value, and a correlation value for each frame of the temporally-filtered robustness set of sub-images and the lung surface mask set of sub-images. Combining the first lung tracking data and the second lung tracking data to create stage combination data may further include providing a displacement, strain, and correlation set forming the second lung tracking data, the displacement, strain, and correlation set forming the second lung tracking data including a displacement value, a strain value, and a correlation value for each frame of the temporally-filtered precision set of sub-images and the lung surface mask set of sub-images. Combining the first lung tracking data and the second lung tracking data to create stage combination data may further include calculating a robustness weighting value for each frame of the temporally-filtered robustness set of sub-images and the lung surface mask set of sub-images from a robustness stage correlation magnitude and robustness predetermined threshold limits. Combining the first lung tracking data and the second lung tracking data to create stage combination data may further include calculating a precision weighting value for each frame of the temporally-filtered precision set of sub-images and the lung surface mask set of sub-images from a precision state correlation magnitude and precision predetermined threshold limits. Combining the first lung tracking data and the second lung tracking data to create stage combination data may further include combining the first lung tracking data and the second lung tracking data using the robustness weighting value and the precision weighting value.

In some arrangements, quantifying displacement and strain based on the tissue tracking data and the stage combination data may include iteratively selecting a frame pair from the time series of ultrasound images of the lung surface, calculating correlation between the frame pair, and storing the resulting correlation images, wherein after an initial iteration, calculating correlation between the frame pair includes a previous displacement estimate in a track direction. Quantifying displacement and strain based on the tissue tracking data and the stage combination data may further include applying a pixel mask based on maximum strain to the stored resulting correlation images, combining the pixel mask based on maximum strain with a pixel selection mask and applying the combined pixel mask and pixel selection mask to the stored resulting correlation images, applying a correlation temporal filter to the stored resulting correlation images, and calculating displacement and strain from the stored resulting correlation images that underwent the combined pixel mask and pixel selection mask and the correlation temporal filter.

In some arrangements, calculating correlation may include selecting a frame pair from the time series of ultrasound images of the lung surface, applying an inter-frame displacement estimate to one image of the frame pair to create a resample image, applying a spatial low-pass filter to the resample image, applying a down sample pixel decimation set to create a down sampled image pair, applying a synthetic frequency filter to the down sampled image pair, and calculating correlation for each pixel in the down sampled image pair.

In some arrangements, applying a pixel mask based on max strain may include providing a correlation image from the stored resulting correlation images. Applying a pixel mask based on max strain may further include performing an iterative process comprising determining a length of the correlation image, using the length of the correlation image and a maximum inter-frame strain threshold to calculate a maximum expected phase offset, using the correlation image to calculate an average phase, and using the average phase and a zero lag covariance of the correlation image to calculate a phase offset from average. The iterative process may further include, from the maximum expected phase offset and the phase offset from average, identifying pixels below a threshold, when a total number of the pixels is less than or equal to the threshold, increasing the threshold and calculating a new maximum inter-frame strain threshold for use in subsequent iterations of the iterative process, and when a number of the pixels is not greater than the threshold, completing the pixel mask for the correlation image.

In some arrangements, calculating displacement and strain from correlation may include iteratively selecting a frame from the stored resulting correlation images that underwent the combined pixel mask and pixel selection mask and the correlation temporal filter, and from the selected frame, calculating a phase angle of a weighted spatial average of a lag=0 correlation image, calculating a weighting for each pixel, calculating a weighted spatial average of a lag=1 correlation image and a lag=−1 correlation image, calculating a phase angle per pixel, calculating strain, calculating displacement, and calculating correlation that is the magnitude of the weighted spatial average of the lag=0 correlation image.

In some arrangements, calculating displacement and strain from correlation may include iteratively selecting a frame from the stored resulting correlation images that underwent the combined pixel mask and pixel selection mask and the correlation temporal filter, and from the selected frame, calculating a phase angle of a weighted spatial average of a lag=0 correlation image, calculating a weighting for each pixel, calculating a weighted spatial average of a lag=1 correlation image and a lag=−1 correlation image, calculating a phase angle per pixel, calculating strain, calculating displacement, and calculating correlation that is the magnitude of the weighted spatial average of the lag=0 correlation image.

In some arrangements, calculating strain may include, from the selected frame, calculating an average phase of each half image, calculating differential motion from a phase angle of a weighted spatial average of a lag=0 correlation image of each half image and the phase angle per pixel, calculating the correlation 1-D center of mass, splitting the selected frame at the correlation 1-D center of mass into a right image half and a left image half, calculating a 1-D center of mass for the right image half and calculating a 1-D center of mass for the left image half, and calculating strain from the 1-D center of mass for the right image half and the 1-D center of mass for the left image half.

BRIEF DESCRIPTION OF THE DRAWINGS

The figures described below depict various aspects of the system and methods disclosed herein. It should be understood that each figure depicts an embodiment of a particular aspect of the disclosed system and methods, and that each of the figures is intended to accord with a possible embodiment thereof. Further, wherever possible, the following description refers to the reference numerals included in the following figures, in which features depicted in multiple figures are designated with consistent reference numerals.

DETAILED DESCRIPTION

The present application describes techniques to measure lung motion using a correlation phase-based method on ultrasound images of the lung surface. In particular, local lung motion and local lung ventilation are measured. Ultrasound imaging and measurement of the lung surface is difficult since the lung surface produces reflected signals that can have large contributions of noise and artifact. Ultrasound signals do not enter normal lung tissue, so any signal projecting into the lung on an ultrasound image is produced by multiple reflections at, and from, the most superficial lung/soft-tissue boundary. With the present techniques, we demonstrate that ultrasound signals can nonetheless be compared at different times and at different locations to assess motion and longitudinal strain of the lung surface. More specifically, the present techniques use the phase of ultrasound signal correlations to assess lung motion (e.g., local lung motion and local lung ventilation).

Figure 1:
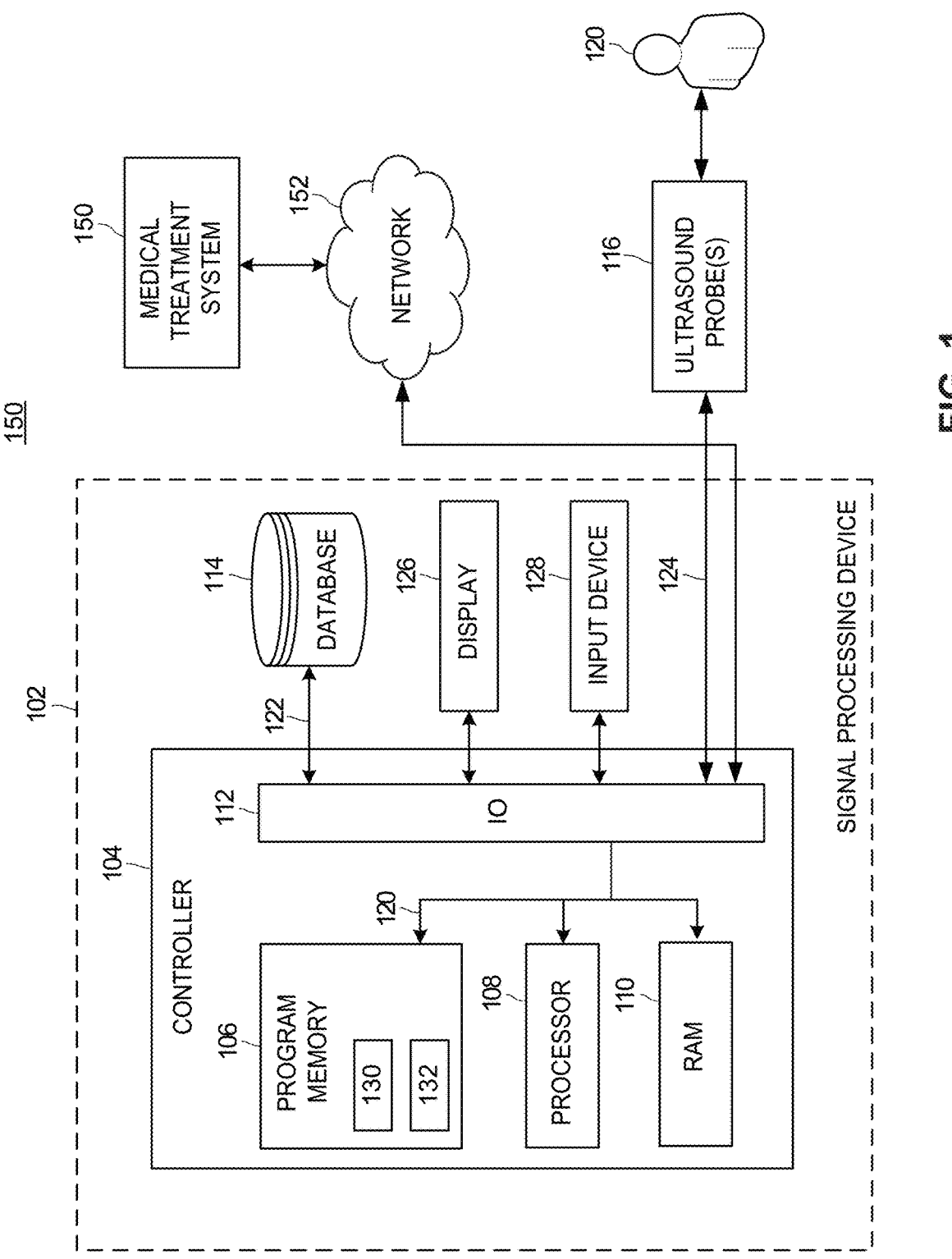
FIG. 1 illustrates an ultrasound imaging system configured to assess lung motion and longitudinal strain, in accordance with an example.

FIG. 1 is an example block diagram of an example lung motion analysis system 100, illustrating the various components used in implementing an example embodiment of an ultrasound imaging system. A signal-processing device 102 (or "signal processor") may be configured to examine a patient 120 via one or more ultrasound probes 116 in accordance with executing the functions of the disclosed embodiments. The signal-processing device 102 may have a controller 104 operatively connected to the database 114 via a link 122 connected to an input/output (I/O) circuit 112. It should be noted that, while not shown, additional databases may be linked to the controller 104 in a known manner. The controller 104 includes a program memory 106, one or more processors 108 (may be called microcontrollers or a microprocessors), a random-access memory (RAM) 110, and the input/output (I/O) circuit 112, all of which are interconnected via an address/data bus 120. It should be appreciated that although only one processor 108 is shown, the controller 104 may include multiple microprocessors 108. Similarly, the memory of the controller 104 may include multiple RAMs 110 and multiple program memories 106. Although the I/O circuit 112 is shown as a single block, it should be appreciated that the I/O circuit 112 may include a number of different types of I/O circuits. The RAM(s) 110 and the program memories 106 may be implemented as semiconductor memories, magnetically readable memories, and/or optically readable memories, for example. A link 124, which may include one or more wired and/or wireless (Bluetooth, WLAN, etc.) connections, may operatively connect the controller 104 to the ultrasound probe(s) 116 through the I/O circuit 112. The ultrasound probe(s) 116 may be operatively connected to the patient 120 at a location corresponding to a sampling region of the patient.

The program memory 106 and/or the RAM 110 may store various applications (i.e., machine readable instructions) for execution by the processor 108. For example, an operating system 130 may generally control the operation of the signal-processing device 102 and provide a user interface to the signal-processing device 102 to implement the processes described herein. The program memory 106 and/or the RAM 110 may also store a variety of subroutines 132 for accessing specific functions of the signal-processing device 102. By way of example, and without limitation, the subroutines 132 may include, among other things: a subroutine for capturing ultrasound images of a patient, a subroutine for identifying a lung surface in the ultrasound images; a subroutine for subsetting the ultrasound images into sub-images; a subroutine for filtering captured ultrasound images by a temporal and/or spatial filter, and a subroutine for determining interframe motion data between captured ultrasound image data (e.g., frames or sub-images).

The subroutines 132 may also include other subroutines, for example, implementing software keyboard functionality, interfacing with other hardware in the signal-processing device 102, etc. The program memory 106 and/or the RAM 110 may further store data related to the configuration and/or operation of the signal-processing device 102, and/or related to the operation of the one or more subroutines 132. For example, the ultrasound image data may be data gathered by the probe(s) 116, data determined and/or calculated by the processor 108, etc. In addition to the controller 104, the signal-processing device 102 may include other hardware resources. The signal-processing device 102 may also include various types of input/output hardware such as a visual display 126 and input device(s) 128 (e.g., keypad, keyboard, etc.). In an embodiment, the display 126 is touch-sensitive, and may cooperate with a software keyboard routine as one of the software routines 132 to accept user input. It may be advantageous for the signal-processing device 102 to communicate with a broader medical treatment system 150 through a network 152, using any of a number of known networking devices and techniques (e.g., through a computer network such as a hospital or clinic intranet, the Internet, etc.). For example, the ultrasound processing system may be connected to a medical records database, hospital management processing system, health care professional terminals (e.g., doctor stations, nurse stations), patient monitoring systems, automated drug delivery systems such as smart pumps, smart infusion systems, automated drug delivery systems, etc. Accordingly, the disclosed embodiments may be used as part of an automated closed loop system or as part of a decision assist system.

Figure 2:
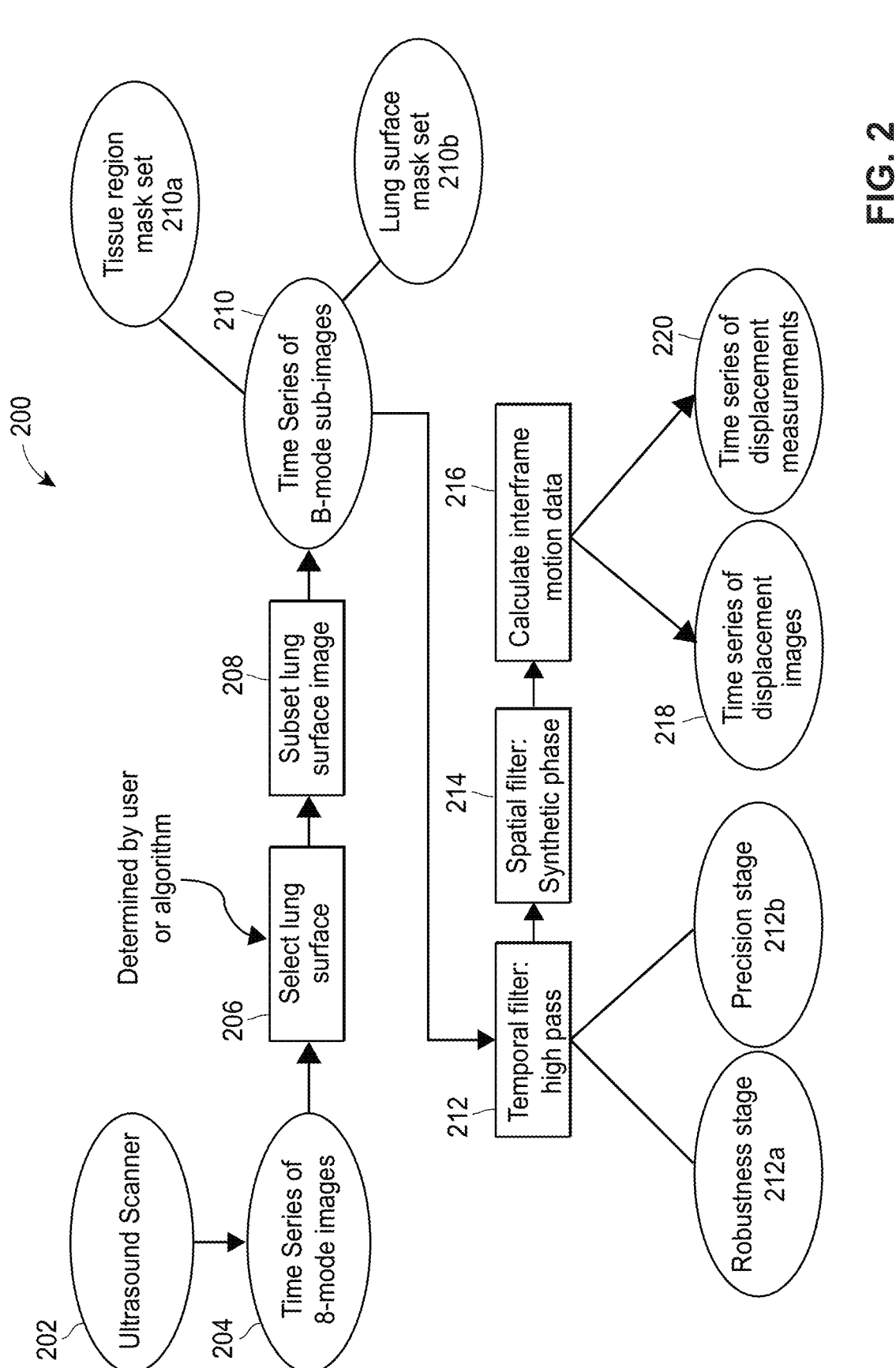
FIG. 2 illustrates a method of estimating lung motion based on an ultrasound signal correlation phase, in accordance with an example.

FIG. 2 shows a method 200 of estimating lung motion. At box 202, an ultrasound scanner (such as ultrasound probe(s) 116 in FIG. 1) is provided. As shown at box 204, the ultrasound scanner is used to acquire a time series of images. The images may be brightness-mode (B-mode) or RF images (including IQ signals, IQ data, and IQ samples). The method could also be applied to 3D ultrasound data, where 2D images containing lung surface are extracted from 3D data. The frame extraction may be optimized by user input or image processing algorithms to select the image plane that captures the largest portion of lung surface and/or portion of lung surface with motion contained in the image plane. The time series includes a plurality of frames, which are input as data into a system for processing. Processing can be done off-line using custom software on a computer after data acquisition is complete. As shown at box 206, a lung surface is identified (either by a user or an algorithm) in one of the plurality of frames. Further details regarding lung surface identification are discussed in conjunction with FIG. 2.

As shown at box 208 of FIG. 2, each of the plurality of frames is subset by a processor into at least one sub-image. This creates a time series of sub-images, as shown in box 210. In some applications of method 200 or other methods discussed below, the time series of sub-images shown in box 210 may have a segmentation algorithm applied to it to create a tissue region mask set 210a and a lung surface mask set 210b (which are a time series of images of the same size and number of frames as the sub-image set shown in box 210). The segmentation algorithm processes each column of each image. Pixels that are higher than a set fraction of the maximum value of each column are identified as lung surface pixels. If the maximum pixel value of a column is below a threshold, the entire column is considered not part of the lung surface (i.e., no pixels in mask=1 for that column). Further details about subsetting each of the plurality of frames into sub-images are discussed in conjunction with FIGS. 3. and 14. As shown at box 212, a high pass temporal filter is applied to each sub-image to reduce an amplitude of signals that arise from specular reflection from the lung surface. This step may not be necessary if the data from the sub-images is high enough quality. Instead of a the high pass temporal filter, a band pass filter or an all pass filter (data passes through) may be used. Alternately, the time series of sub-images may be temporal filtered two or more times using different temporal filters, creating multiple temporal filter time image sets. The multiple temporal filters may include: a robustness stage filter, shown at box 212a, and a precision stage filter, shown at box 212b. Further details about the temporal filter are discussed in conjunction with FIGS. 5A=, 5B, 13A, 13B, 13C, 14, and 16. As shown at box 214, a spatial filter is applied along an x-axis of each sub-image to transform each pixel in each sub-image into data. The data for each pixel includes a real component and an imaginary component. The data is compiled in a complex data set, each complex data set associated with one of the plurality of frames. Further details about the spatial filter are discussed in conjunction with FIGS. 6, 7A, and 7B. As shown at box 216, inter-frame motion data is calculated from the complex data sets associated with one or more pairs of successive frames. Further details about the calculation of inter-frame motion are discussed in conjunction with FIG. 8. The calculation of inter-frame motion may include creating a time series of displacement images, as shown at box 218 and discussed in conjunction with FIG. 9. The calculation of inter frame motion may include creating a time series of displacement measurements, as shown at box 220 and discussed in conjunction with FIG. 10.

Figure 3:
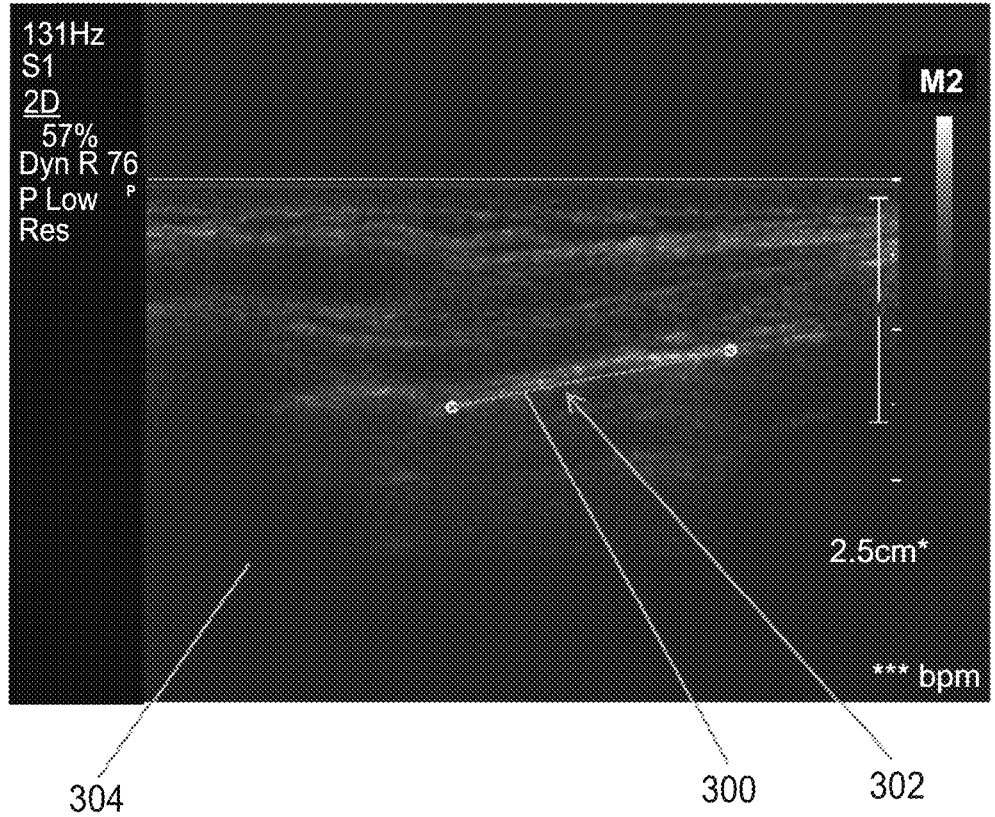
FIG. 3 illustrates identifying a lung surface in an ultrasound image frame, in accordance with an example.

Turning to FIG. 3, lung surface identification by a user on an image frame is shown. Specifically, using custom software on a computer, the user draws a line 300 between a right edge and a left edge of the lung surface 302 in one of the plurality of frames 304. The line 300 could be a piecewise line, a curve, a spline, or so forth. The line 300 could instead be a box, circle, or other closed shape to identify a region used to identify a sub-image 306, as discussed further below. Alternately, the lung surface 302 may be identified in an automated manner by use of an image segmentation algorithm.

Figure 4:
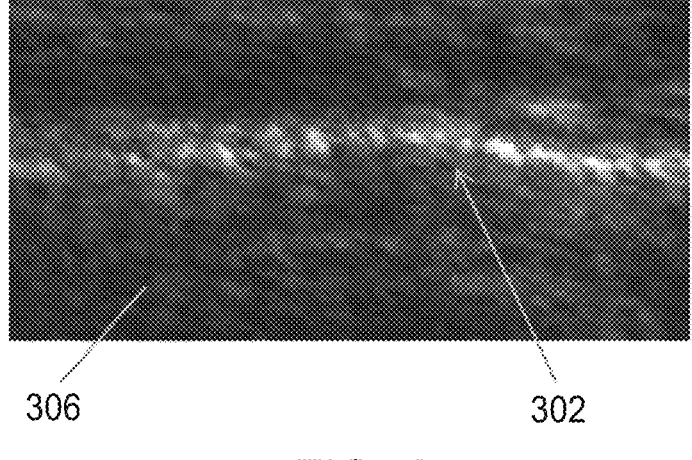
FIG. 4 illustrates subsetting the ultrasound image frame of FIG. 3 into a sub-image.

As shown in FIG. 4, the software of the computer identifies a sub-image 306 based on the identification of the lung surface 302. An image segmentation algorithm may be used to identify the sub-image 306 in an automated manner. A variety of subsetting or region identifying methods could be used to identify the sub-image 306. As an example method, when the user identifies the lung surface 302 by drawing the line 300 (shown in FIG. 3), the sub-image 306 (shown in FIG. 4) may be a sub-image having a fixed number of pixels above the line and below the line 300. The sub-image viewed in one of the plurality of frames 304 may be a parallelogram that, when straightened, results in a rectangular sub-image 306. In the example shown in FIG. 4, a margin of thirty pixels above and below the line 300 drawn by the user (shown in FIG. 3) was taken to create the sub-image 306 (shown in FIG. 4) from the frame 304 on which the user identified the lung surface 302. Other sizes of sub-images 306 having either more or fewer pixels above and below the line 300 are also contemplated as being within the scope of the present disclosure. The sub-image 306 may include the entire frame 304. As shown in FIG. 4, when the sub-image 306 is identified as described based on a line 300 identifying the lung surface 302, the lung surface 302 is arranged approximately along the x-axis of the sub-image 306. For the remaining image frames taken by the ultrasound in the same time series, a sub-image can be identified for each that has the same set of pixels as the sub-image 306 taken from the frame 304 on which the line 300 is drawn. Each of these sub-images will then also have the lung surface 302 arranged approximately along their x-axes. Each sub-image could be adjusted (e.g., scaled or translated) to account for motion of tissues or imaging geometry, and this adjustment could be completed manually by an operator or automatically using a computer vision or image processing method (e.g., a computer process that identifies image motion or ultrasound shadowing).

Figure 5B:
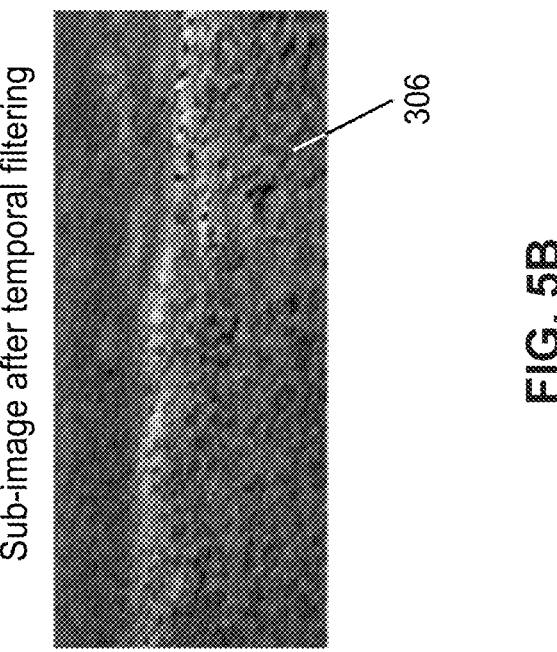
FIG. 5B illustrates the sub-image of FIGS. 4 and 5A after applying the temporal filter.
Figure 5A:
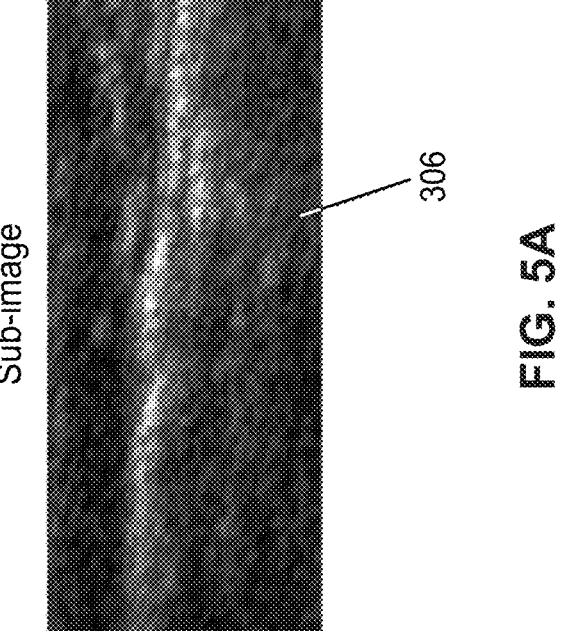
FIG. 5A illustrates the sub-image of FIG. 4 before applying a temporal filter.

The sub-images are then prepared for motion measurement by temporal and spatial filtering. A high pass temporal filter is applied to reduce the amplitude of stationary or slow-moving signals that arise from specular reflection from the lung surface. The processing effectively emphasizes the respiratory motion component of the lung surface signals. FIG. 5A shows the sub-image 306 before temporal filtering (i.e., as original data) and FIG. 5B shows that same sub-image 306 after temporal filtering.

The spatial filter that is then applied to the sub-image 306 is a synthetic phase or a gradient filter. An example of motion estimation using synthetic phase is found in Xunchang Chen, M. J. Zohdy, Emelianov SY and M. O'Donnell, "Lateral speckle tracking using synthetic lateral phase," in IEEE Transactions on Ultrasonics, Ferroelectrics, and Frequency Control, vol. 51, no. 5, pp. 540-550, May 2004, which is incorporated herein by reference in its entirety. The synthetic filter is applied along the x-dimension of the sub-image 306, which is approximately along the direction of the lung surface 302, as discussed above. The spatial filter transforms each pixel of the sub-image 306 into data. The data includes a real component and an imaginary component. The data is compiled in a complex data set. This process is completed for each sub-image (e.g, sub-image 306) of each one of the plurality of frames (e.g., frame 304) such that each of the plurality of frames has a complex data set associated with it as a result of the spatial filtering.

Figure 6:
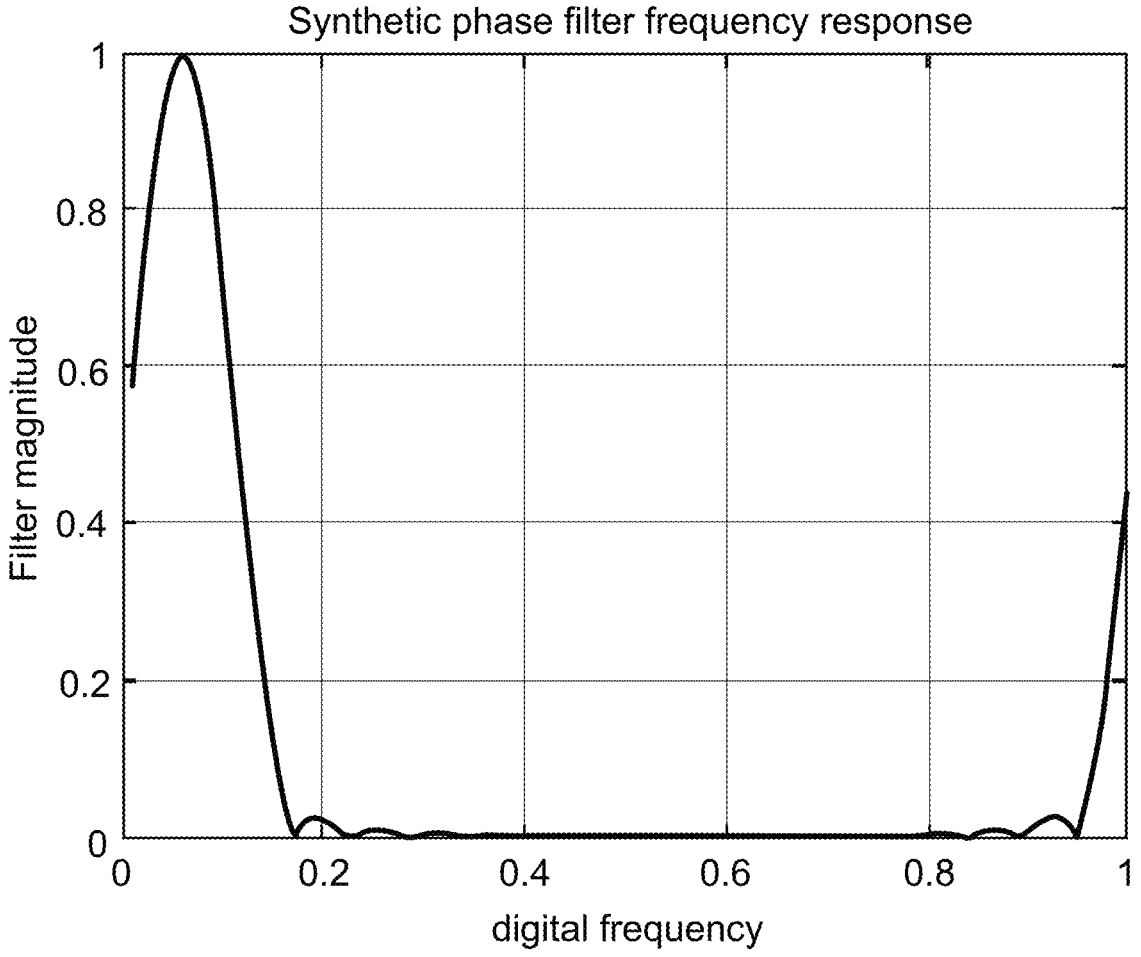
FIG. 6 illustrates a synthetic phase frequency response, in accordance with an example.

More specifically, the phase of the complex signal, defined by atan(imaginary/real), is related to the x-location in the image. The angle change is proportional to distance change in the image with the complication that it repeats through 0–2π. The synthetic phase filter is a complex band pass filter. An example synthetic phase filter frequency response is shown in FIG. 6. Digital frequency shown on the x-axis is the spatial frequency normalized by the sampling frequency which is set by the pixel size of the image. Spatial filtering could also be applied in the y-dimension of the sub-image 306. For example, a low pass spatial filter could be applied along the y-dimension to reduce the impact of motion normal to the lung surface on the longitudinal lung motion measurements enabled by the synthetic phase filter.

Figure 7B:
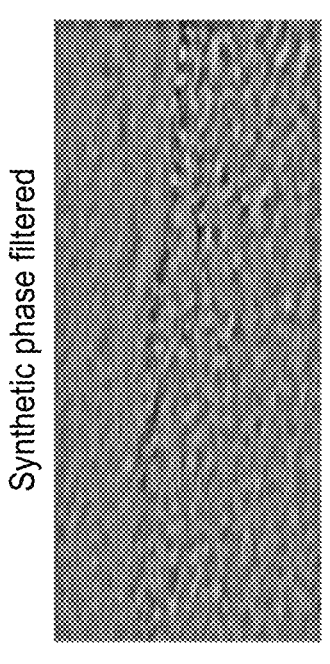
FIG. 7B illustrates the sub-image of FIG. 7A after applying the spatial filter.
Figure 7A:
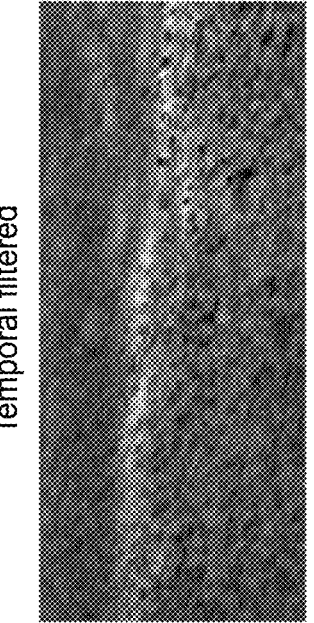
FIG. 7A illustrates the temporally filtered sub-image of FIG. 5B before applying a spatial filter.

The filter synthetic phase filter produces a one-sided band of frequencies about DC. In the spatial domain, the filter creates pulse-range data represented by: $s(x)=A(x-U)e^{-i2\pi f}$ $(x-U)$ (1) where x is digital spatial coordinate and U is the position of the signal. The synthetic phase filter characteristics determine the signal amplitude profile A(x−U) and the spatial center frequency, f, of the complex signal. The signal represented as one dimensional, since the filtering is done independently on each row of the image. FIGS. 7A and 7B show the effect of the synthetic phase filter. FIG. 7A shows the temporally filtered sub-image 306 prior to spatial filtering. FIG. 7B shows the sub-image 306 after spatial filtering. The real component of the complex image is displayed. Note the wave texture produced, as expected per equation 1.

Figure 8:
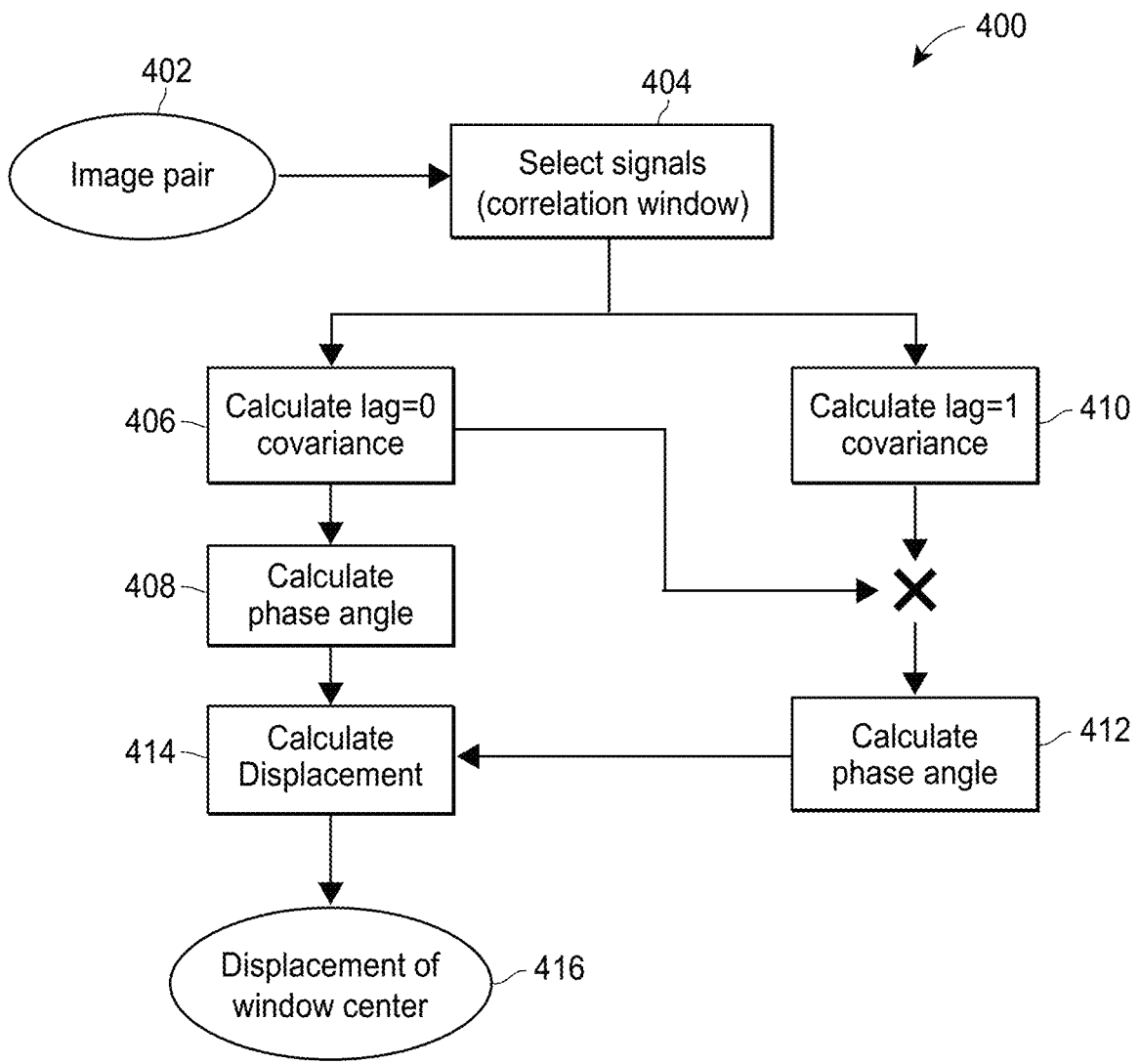
FIG. 8 illustrates a method of calculating displacement by processing images from successive frames, in accordance with an example.

FIG. 8 shows a method 400 for calculating inter-frame motion (box 216 of FIG. 1) between two images or subimages of the plurality of frames. At box 402, an image pair is identified. At box 404, signals are extracted from same location, called the correlation window or window location, in each image. For example, consider two signals from successive frames:

$$s_1(x)=A_1(x-U_1)e^{-i2\pi f(x-U_1)} \tag{2}$$

$$s_2(x)=A_2(x-U_2)e^{-i2\pi f(x-U_2)} \tag{3}$$

where s1 and s2 are signals from frames 1 and 2, respectively. The positions of the signals are given by U1 and U2.

The goal of the motion measurement is to determine the movement of the signal, and therefore the lung surface motion, between frames. The inter-frame motion is represented by U2−U1. The first part of the calculation is the sum of the complex conjugate multiply of the two signals:

$$\sigma(0) = \tag{4}$$
$$\sum_{x} s_2(x) * s_1^*(x) = \sum_{x} A_2(x - U_2)e^{-i2\pi f(x-U_2)}A_1(x - U_1)e^{i2\pi f(x-U_1)}.$$

Equation 4 presented above is the zero lag covariance of $s_1$ and $s_2$, or equivalently the numerator of the zero lag cross correlation, which is shown at box 406 in FIG. 8. The range of the sum of pixels (x) defines the covariance window or kernel. In practice, this is a neighborhood of pixels around the pixel of interest. For example, to produce a local, fine resolution measurement of displacement, a small window may be used (e.g., 5×5 pixels). Alternatively, the window can be the size of the sub-image to produce the displacement for the entire image. Similarly, the window can be the right or left half of the image, to produce a displacement of the right or left half of the image, respectively. The split image measurement (right and left halves) can be used to calculate strain of the lung surface across the subset, as related to FIG. 11.

Calculating the phase angle of the covariance of equation 4, shown at box 408 in FIG. 8, yields:

$$\text{angle } (\sigma(0)) = \text{angle } (s_2(x) * s_1^*(x)) = 2\pi f(U_2 - U_1) \tag{5}$$

which is also the phase angle of the correlation of signals s1 and s2. Equation (5) is proportional to the signal motion, but the measurement is in units of phase (e.g. radians), not pixels.

To convert to pixels, the value of $2\pi f$, or equivalently the phase change per pixel motion, must be calculated. This is done by first calculating the lag 1 covariance of s1 and s2, as shown at box 410 in FIG. 8. Equivalently, this is the complex conjugate multiply with s1 shifted by 1 pixel:

$$\sigma(1) = \sum_{x} s_2(x - 1) * s_1^*(x) = \tag{6}$$
$$\sum_{x} A_2(x - 1 - U_2)e^{-i2\pi f(x-U_2-1)}A_1(x - U_1)e^{i2\pi f(x-U_1)}.$$

While lag 1 covariance is described as being used, a similar approach could be used with lag-1 covariance or a combination thereof. Higher order lags (e.g., 2, −2) could be used or used in combination.

At box 412 of FIG. 8, the phase angle of the complex conjugate multiply of the lag 0 and lag 1 covariances is calculated:

$$\text{angle}(\sigma(1)\sigma^*(0))=2\pi f \tag{7}$$

which produces $2\pi f$, or equivalently, phase angle per pixel motion. In overview, this approach induces a known shift between the images to extract the phase change associated with the shift.

At box 414 of FIG. 8, the motion between the signals in pixels, ΔU1,2, is equation (5) normalized by equation:

$$\Delta U_{1,2} = 2\pi f(U_2 - U_1)/2\pi f \qquad (8).$$

This calculation is done for every window location in the image and for every frame pair. At box 416, the result of these displacement calculations is assigned to the window center. For example, a series of window locations can be defined, each centered on each pixel of the image to create a displacement image, with the result that there will be a displacement value for each pixel. Alternatively, the window location could be the entire sub-image, right half of the sub-image, or left half of the sub-image. In that case, a single displacement value is created for the large region. The large region approach is more robust to noise and artifacts compared to the former approach described of averaging the displacements from a displacement image. The process of specifically calculating a strain measurement using this methodology is discussed further below.

Figure 9:
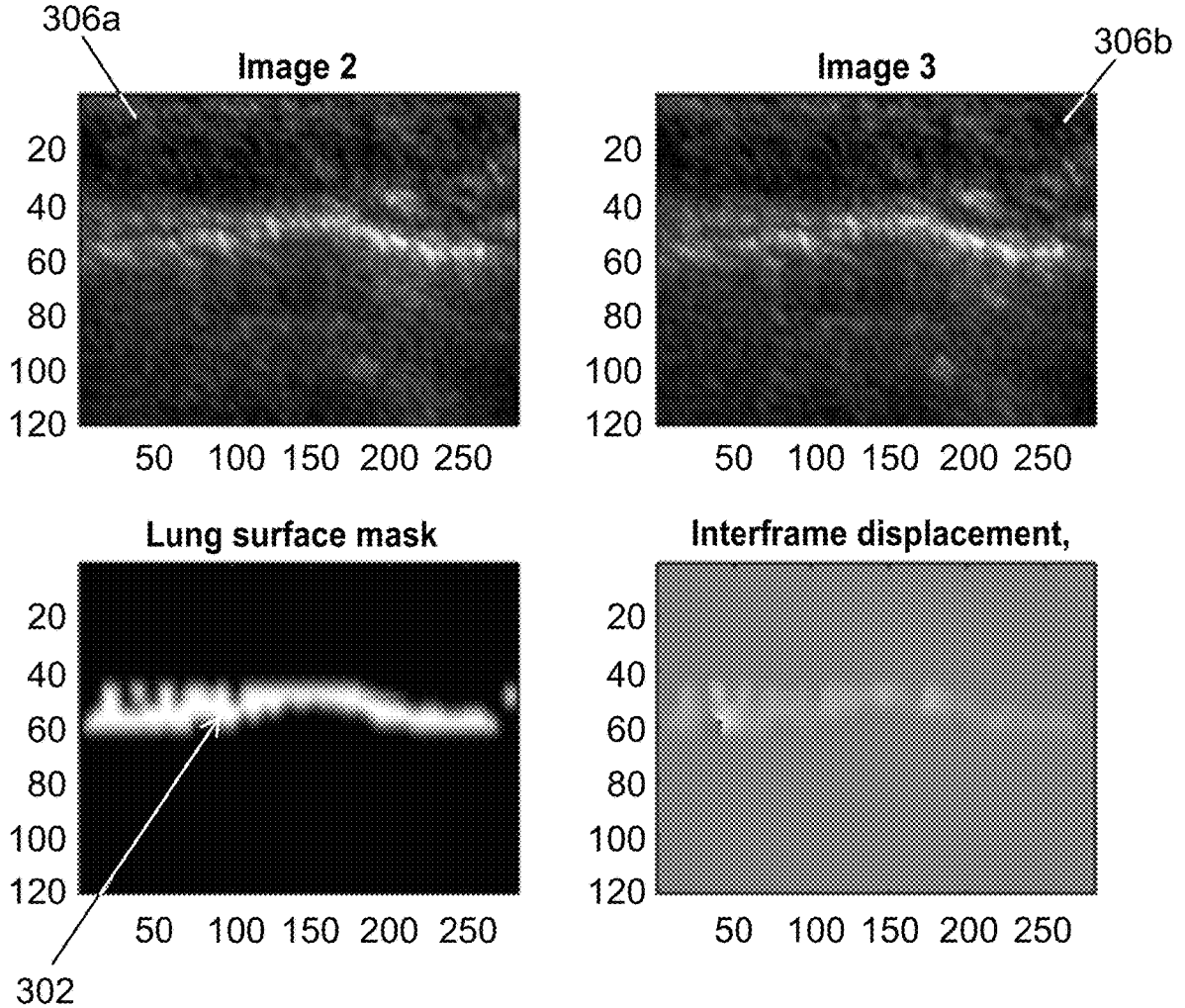
FIG. 9 illustrates a sample result from a motion measurement using correlation phase, in accordance with an example.

Since not all pixels in a sub-image (such as sub-image 306) correspond to the lung surface (such as lung surface 302), a segmentation algorithm is applied to identify pixels from the lung surface 302. Only the lung surface pixels are used to calculate the lung motion and for motion display purposes, as shown in FIG. 9. The top two images in FIG. 9 show two sub-images 306a and 306b used for calculating motion. The lower left image in FIG. 9 is the pixels corresponding to the lung surface 302. In this case, white indicates lung surface 302. In the current invention, the lung surface 302 is identified by locating pixels whose value is above a predefined fraction of the maximum pixel in each column. Effectively, this algorithm selects the brightest pixels in each column which corresponds to the lung surface 302. Other approaches could also be used to achieve effective segmentation. Finally, the lower right image shows the motion of each pixel (i.e., displacement image for frame pair 2,3). The dynamic range of the image is +/−5 pixels of motion in along x. White is 5 pixels motion along +x (i.e., to the right on the image) and black is 5 pixels motion along −x (i.e., to the left on the image).

Figure 10:
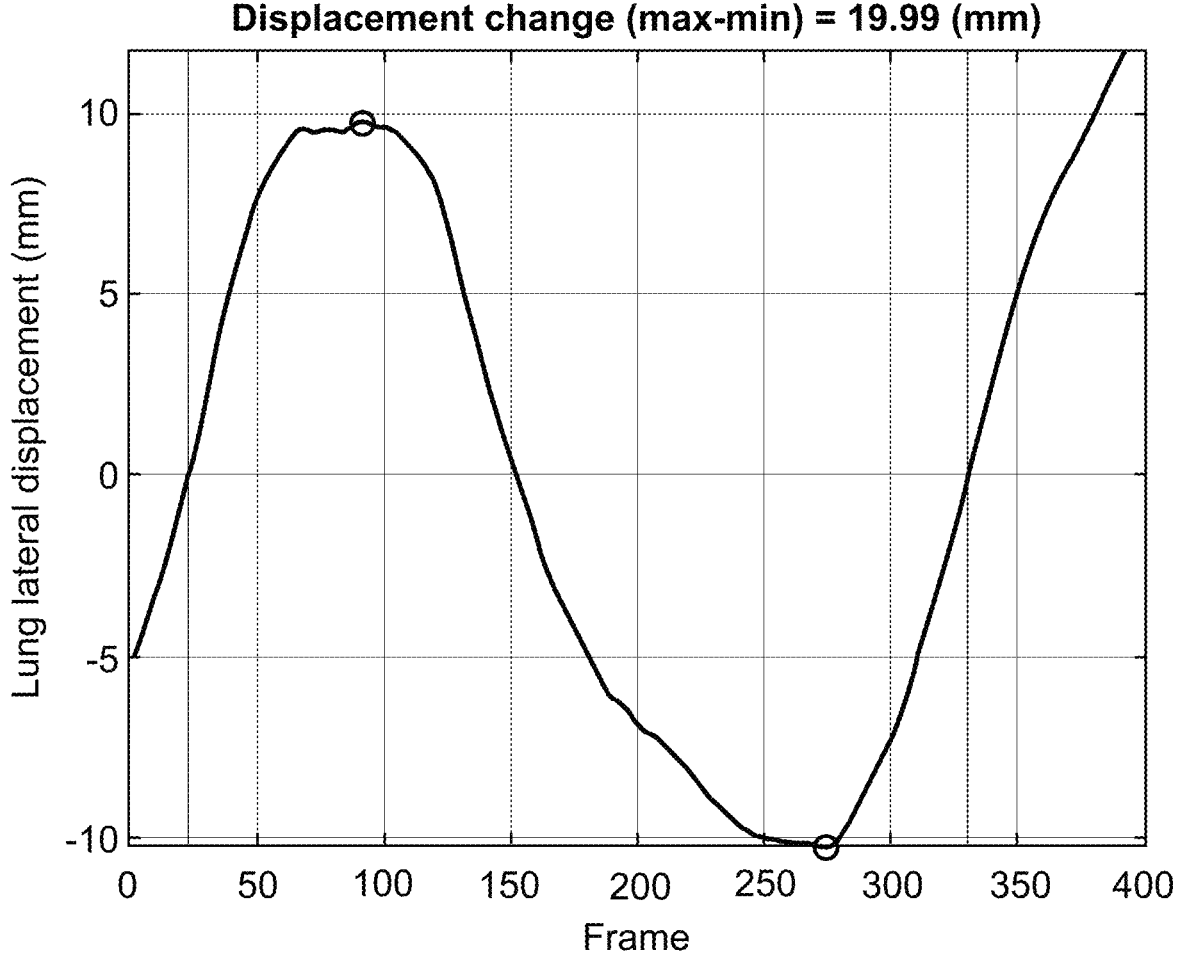
FIG. 10 illustrates a measurement of lung surface lateral displacement over time (i.e., frames), in accordance with an example.

In addition to motion images, the total motion for the entire image is calculated using equation 8, as described previously. In this case, a single window is used for covariance calculations, in contrast to the multiple windows about each image pixel used for the displacement image shown in FIG. 9. The single window pixels are the lung surface pixels defined by the segmentation algorithm described above. An example full frame motion measurement is shown in FIG. 10. The plot in FIG. 10 represents the lung surface displacement for each frame. The oscillation represents cyclical motion from inhalation and exhalation. In FIG. 10, the motion of the lung between full inhale and exhale is 19.99 mm.

Figure 11:
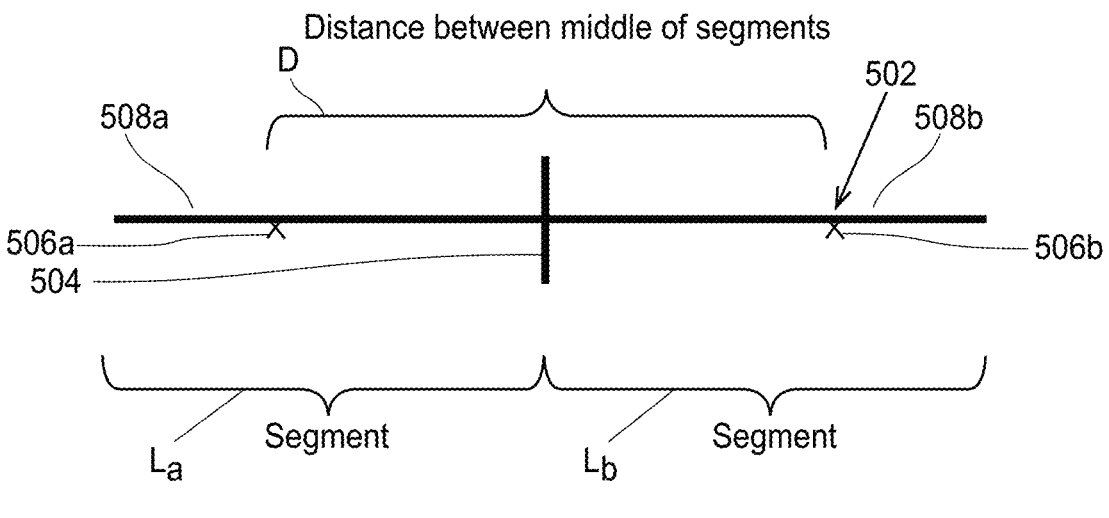
FIG. 11 schematically illustrates a lung surface and a method of calculating instantaneous strain of the lung surface, in accordance with an example.

FIG. 11 shows a schematic of lung surface 502 which is divided in half (identified by marker 504) with the center position of each half marked by an "x" (identified as 506a and 506b). Each half of the lung surface 502 forms a segment, resulting in two segments 508a and 508b having respective lengths $L_a$ and $L_b$ shown by the lower blue brackets. The distance D between the center positions 506a and 506b of each segment 508a and 508b is shown by the upper black bracket. The mean displacements of each segment 506a and 506b are subtracted and divided by the distance D to get instantaneous strain. Similarly, a frame may be separated into more than two segments to get multiple strain measurements across the image. For example, right, left, and middle segments can produce two strain measurements (right-middle, middle-left).

Figure 12:
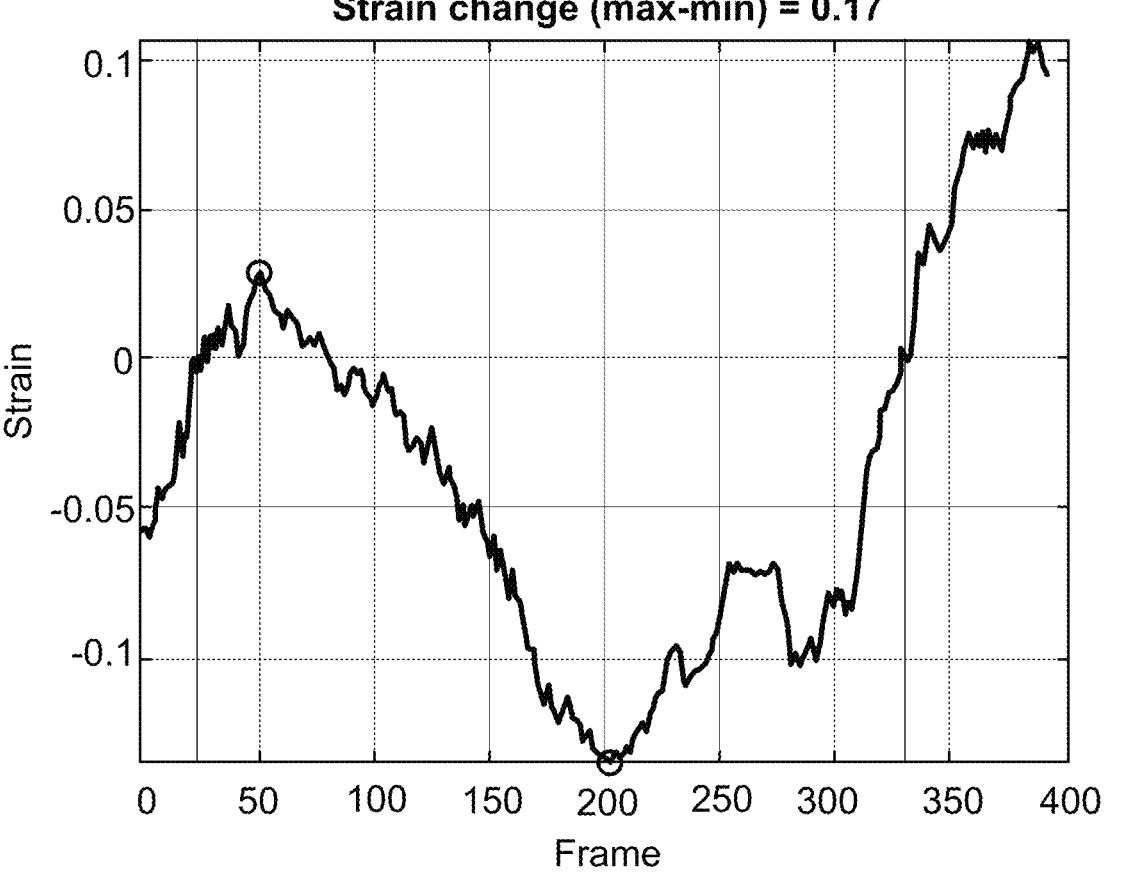
FIG. 12 illustrates a measurement of lung surface longitudinal strain over time (i.e., frames), in accordance with an example.

The instantaneous strain can be calculated for each of the plurality of frames in order to track the change in instantaneous strain over time, where time correlates with a number of successive frames. Strain, displacement, and strain rate measurements can be done over a breath cycle, defining the set of frames to determine a minimum, maximum, average, and so forth. A breath cycle may be defined by minimum and maximum displacement or other data, such as surrounding tissue motion tracked by ultrasound, external bellows, or ventilator signals. For example, FIG. 12 shows a measurement of lung surface longitudinal strain over approximately 400 frames. The approximately 400 frames were taken over the period of time in which a subject upon which the ultrasound was being performed took a full breath. By subtracting the minimum strain from the maximum strain, the lung strain from a full breath is determined to be 17%. This strain could be compared to target or expected strain amounts for a full breath to assess local lung ventilation. Assessing local lung ventilation allows accurate assessment of positive end-expiratory pressure (PEEP). As discussed in the background section above, an inability to assess PEEP is one of the major difficulties in ventilator management, and one of the biggest problems faced with ventilator sharing. Thus the disclosed method of calculating strain improves ventilator management and enables ventilator sharing. In addition to minimum-maximum strain determinations, other metrics could also be calculated, such as average strain minus minimum strain, or strain rate (temporal difference of strain).

Figure 13A:
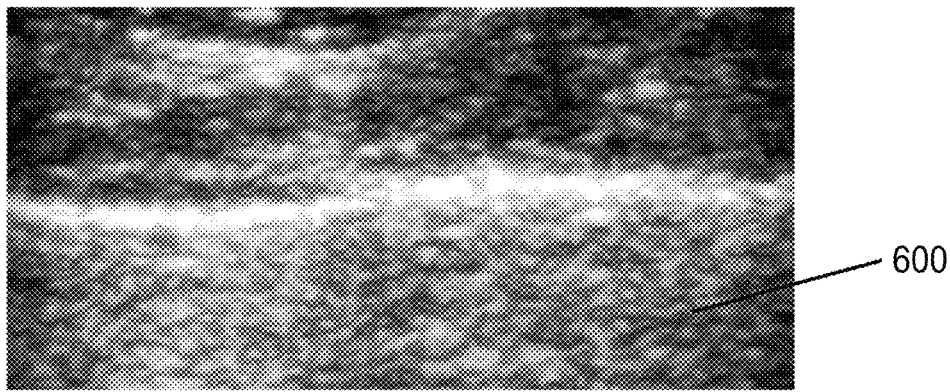
FIG. 13A illustrates a second sub-image different than the sub-image of FIG. 5A before applying a temporal filter.
Figure 13B:
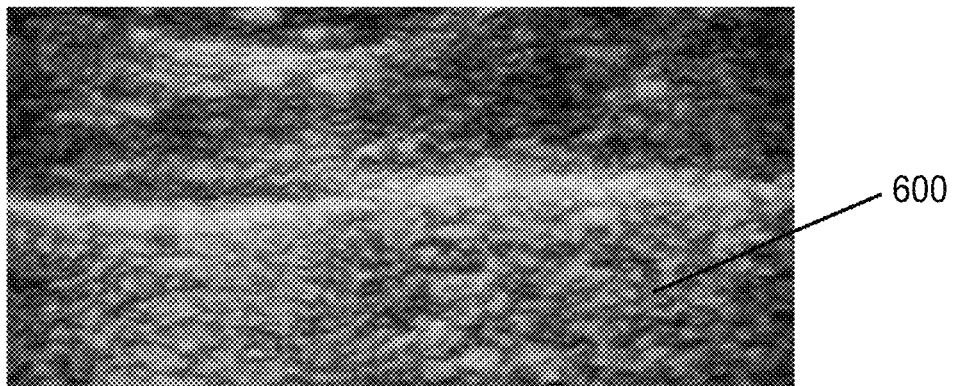
FIG. 13B illustrates the second sub-image after completing the robustness stage of the temporal filter.
Figure 13C:
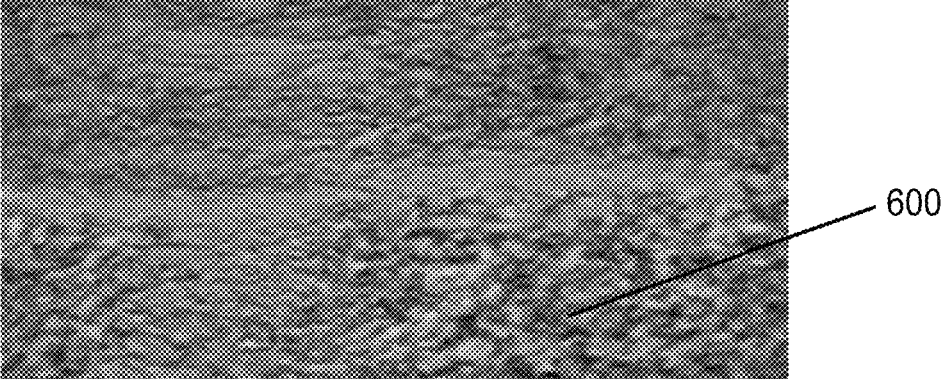
FIG. 13C illustrates the second sub-image after completing the precision stage of the temporal filter.

FIGS. 13A-13C illustrate a lung surface sub-image 600, similar to sub-image 306 discussed above. In FIG. 13A, the lung surface sub-image 600 has not yet undergone temporal filter (shown in box 212 in FIG. 2). In FIG. 13B, the lung surface sub-image 600 has gone through the robustness stage temporal filter (shown at box 212a in FIG. 2). In FIG. 13C, the lung surface sub-image 600 has gone through the precision stage temporal filter (shown at box 212b in FIG. 2).

Figure 14:
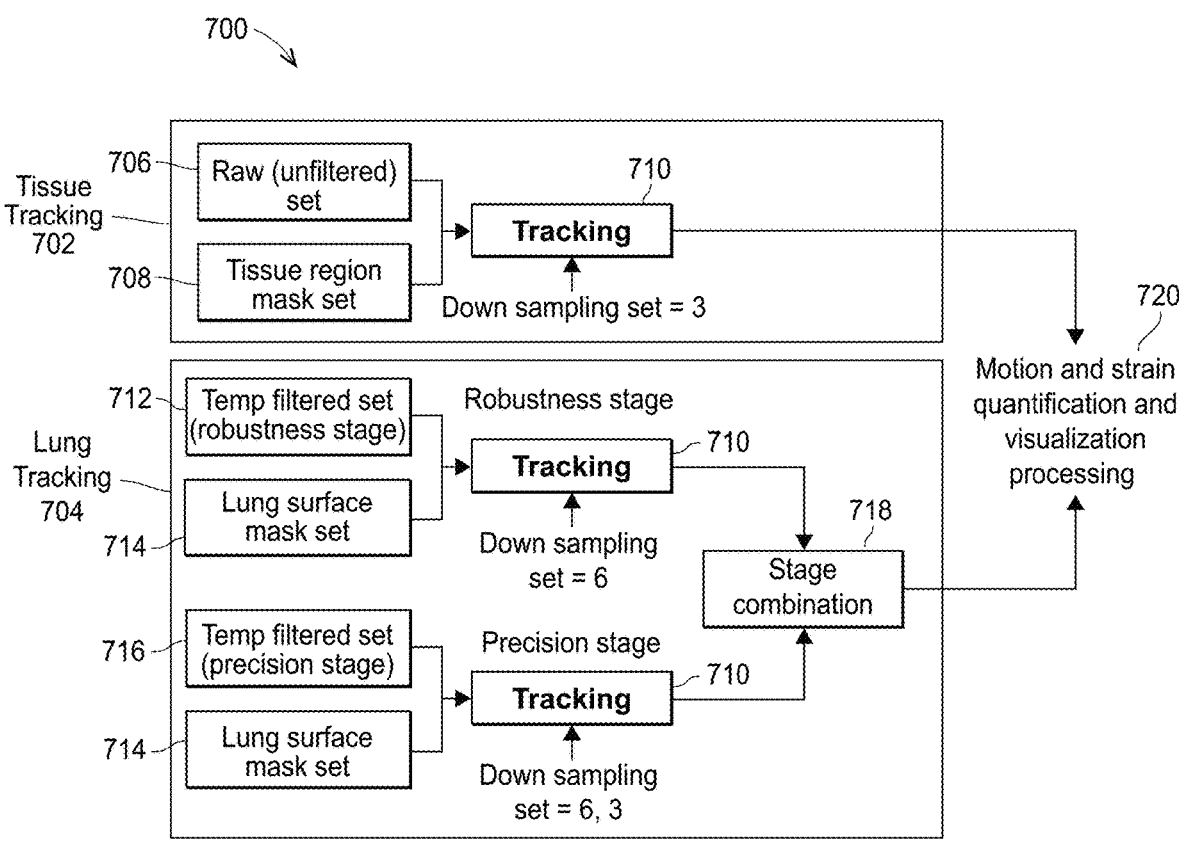
FIG. 14 illustrates a method of motion and strain quantification and visualization processing, in accordance with an example.

FIG. 14 illustrates a method 700 for estimating lung motion. The method 700 includes performing tissue tracking, shown within box 702, and lung tracking, shown within box 704. Tissue tracking, shown within box 702, uses a raw (unfiltered) set of images shown at box 706 and a tissue region mask set shown at box 708 (such as tissue region mask set 210a illustrated in FIG. 2) in a tracking method 710, which is discussed in greater detail in FIG. 15. Lung tracking, shown within box 704, uses a set of images that has been temporally filtered with a robustness stage filter (e.g., robustness stage filter 212a in FIG. 2) shown at box 712 and a lung surface mask set (such as lung surface mask set 210b illustrated in FIG. 2) shown at boxes 714 in the tracking method 710. Lung tracking further uses a set of images that has been temporally filtered with a precision stage filter (e.g., precision stage filter 212b in FIG. 2) shown at box 716 and the lung surface mask set (such as lung surface mask set 210b illustrated in FIG. 2) shown at boxes 714 in the tracking method 710. The tracking method 710 may use different spatial down sampling for tissue tracking 702 and lung tracking 704. The robustness and precision stages may use different spatial down sampling values. The down sampling is preferably done by spatial low pass filtering, shown by box 1106, and down sampling or pixel decimation, shown by box 1108, the image frames of the image set (raw or temporally filtered image set). Additionally, the lung tracking precision stage may utilize two down sampling stages. In this case, the displacement measurements from the first down sampling stage (=6 shown in FIG. 14) are used to resample the image data, shown at box 1104. The resampled images are used for the second down sampling stage (=3 shown in FIG. 14), shown in FIG. 15. The tissue tracking and lung tracking robustness stages down sampling are preferably 3 and 6, respectively, but can be any down sampling values providing suitable tracking performance. Lung tracking then involves combining the tracking results in a stage combination method 718, which is discussed in greater detail in FIG. 16. Ultimately, the results of tissue tracking and lung tracking are combined to provide motion and strain quantification and visualization processing, shown at box 720. Lung tracking is a primary function of the invention. However, a major issue that arises during respiration assessments using lung tracking is what are the boundaries of each breath. Soft-tissue motion often has a periodicity that corresponds to the respirations, and given the fact that the noise in the soft-tissue tracking is not magnified by the lung-soft-tissue interface, correlation coefficients generated in soft-tissue tracking can be much higher than those generated in lung surface tracking. This permits much better, cleaner definitions of rapid/high-frequency temporal changes in motion that occur during respiration, such as at the beginning and end of breaths. Defining the temporal limits of breaths is critical in estimating displacements and strains during breathing. Soft-tissue motion tracking can define these critical limits.

The combination of the temporal filter and spatial down sampling determine the spatial and temporal frequencies of the image sets used for tracking. Adjusting the characteristics of the temporal filter such as bandwidth, stop band gain and center frequency, along with the down sampling value, provides control of tracking precision and robustness. For example, larger image features are tracked using larger down sampling in the robustness stage, which may reduce tracking noise if image spatial frequency content is band limited about DC (direct current, spatial frequency=0) or the image data is spatially oversampled. Precision stage temporal filtering has higher filter center frequency and lower stop band gain compared to robustness stage temporal filtering. This results in higher velocity tissue motion more favorably tracked by the precision stage compared to robustness stage at the expense of greater high frequency (both spatial and temporal) noise sensitivity. Therefore down sampling and associated low pass filtering control: (1) spatial frequencies (e.g., image feature size and sharpness) used for tracking, (2) signal to noise ratio of tracked images by spatial banding limiting the image data, and (3) detting the tracking range (i.e., maximum inter-frame displacement than can be measured) by determining the effective pixel size.

The invention described by FIG. 14 has tissue and lung tracking processing paths. The lung tracking processing has both robustness and precision stages, providing course, but noise robust motion measurements and precise but more noise sensitive measurements, respectively. Alternatively, lung tracking processing could be done without tissue tracking. Also, the lung tracking or tissue tracking could be done with any number of stages that are ultimately combined (if more than one) in a manner similar to robustness and precision stages shown in FIG. 14 or using a single stage. The down sampling, temporal filter parameters, pixel masks and other algorithm parameters are not limited to those shown in FIG. 14, and any suitable values or data may be used.

Figure 15:
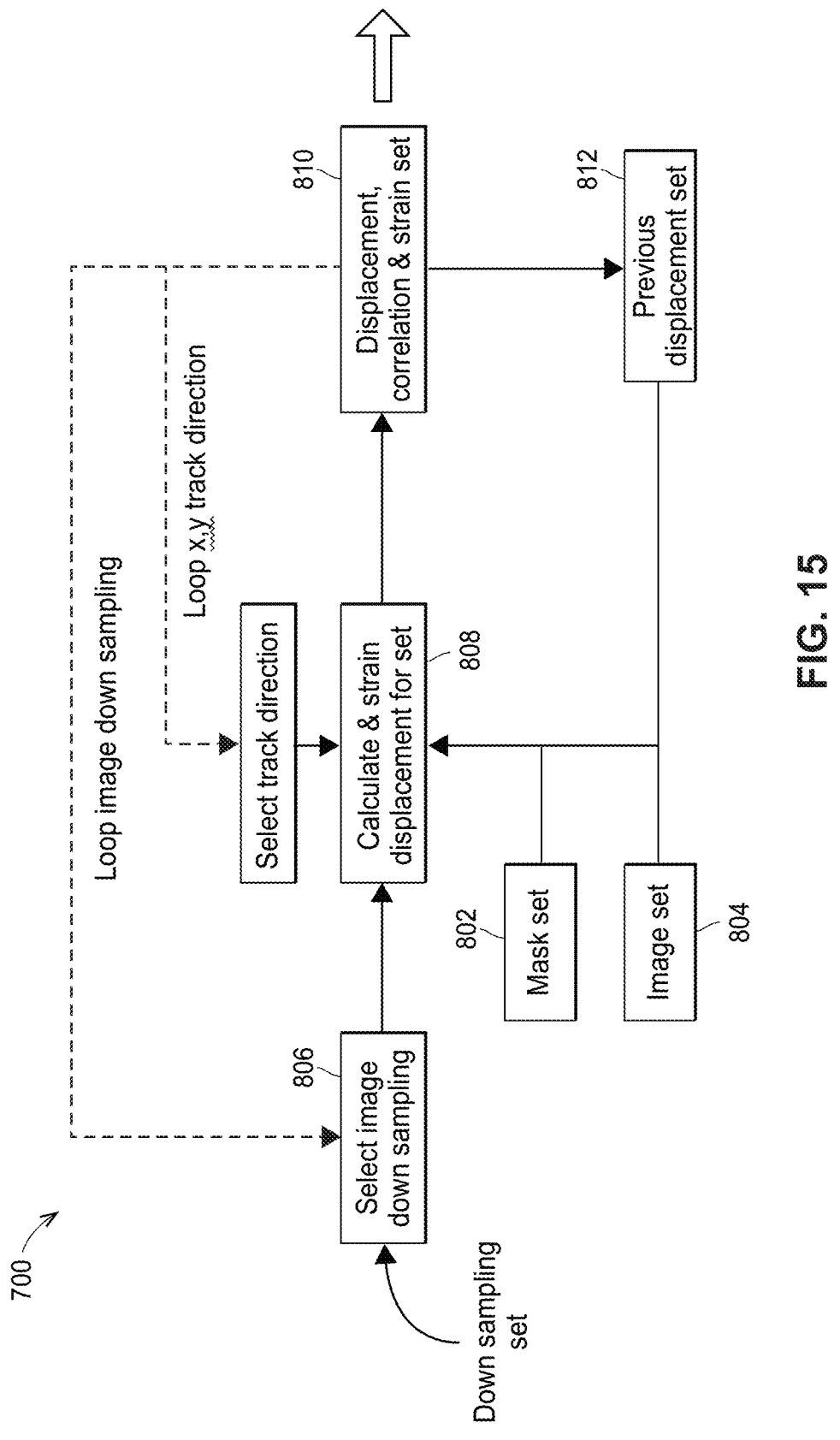
FIG. 15 illustrates a method of tissue and/or lung tracking utilized in conjunction with the method of FIG. 14, in accordance with an example.

FIG. 15 illustrates the tracking method 710 of FIG. 14. The inputs to the tracking stage 710 are the image set and mask set, shown at boxes 802 and 804 respectively, and down sampling parameter value(s) shown at box 806. These differ depending on tracking stage as shown in FIG. 14. For example, lung tracking robustness stage uses: image set=temporally filtered set (robustness filter), mask set=lung surface mask set, and down sampling set=6. The tracking process is controlled by the down sampling factor, shown at box 806. Additionally, the image and mask sets are used to calculate strain and displacement for the set, shown at box 808 and is further illustrated by FIG. 17. The outputs of this processing are a displacement set, strain set and correlation set, shown by box 810. For each down sample value, the displacement and strain are calculated in both the x and y directions (shown in the "select track direction" box 814) as indicated by FIG. 15. The strain is the normal strain component of the strain tensor. For tracking stages with multiple down sampling values in down sampling set, like the lung tracking precision stage, the tracking process of FIG. 15 is repeated. In this case, the 'Calculate strain and displacement for set processing', box 808, utilizes the displacement measurements calculated from the previously executed down sampling value shown at box 812. That is, for stages that use more than one down sampling value, the tracking outputs of the second and subsequent stages rely on the tracking output of the preceding stage. For example, the 'lung tracking precision stage' displacement set calculated using down sample=6 are used for calculating displacement, strain and correlation sets for the down sample=3 tracking execution, along with the mask and image sets.

Figure 16:
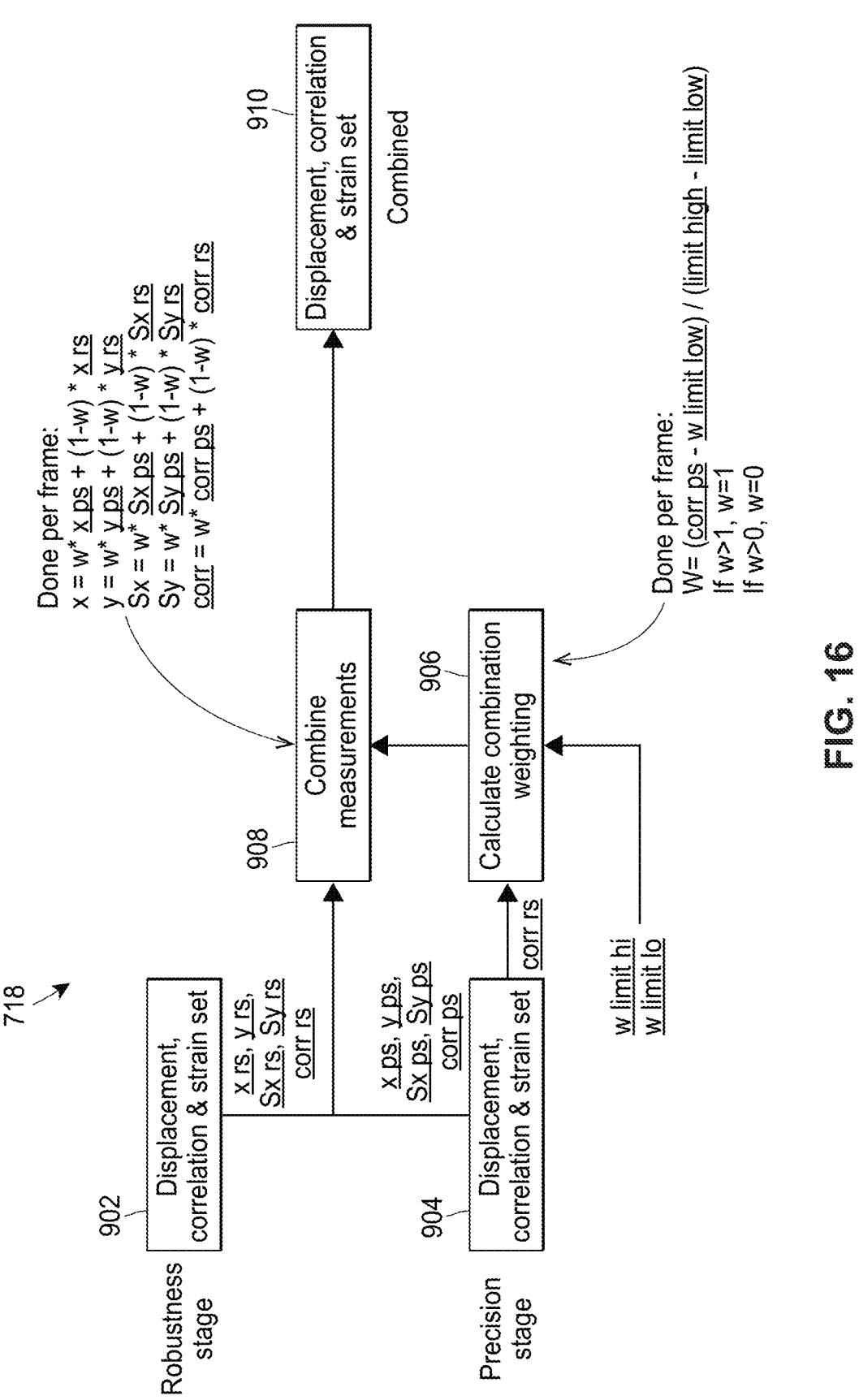
FIG. 16 illustrates a method of stage combination utilized in conjunction with the method of FIG. 14, in accordance with an example.

FIG. 16 illustrates the stage combination method 718 of FIG. 14. The output of tracking 710 is displacement, correlation and strain sets, represented by box 810 of FIG. 15. These outputs for the robustness and precision lung tracking stages are represented by boxes 902 and 904, respectively, shown in FIG. 16. The output sets of the robustness stage may be described by the variables:
x_rs=x displacement
y_rs=y displacement
Sx_rs=x strain
Sy_rs=y strain
corr_rs=correlation magnitude
Similarly for the precision stage:
x_ps=x displacement
y_ps=y displacement
Sx_ps=x strain
Sy_ps=y strain
corr_ps=correlation magnitude.
Note that each of these variables has a value for each frame (i.e., displacement, strain and correlation measurements for each frame of the image set). A weighting value is calculated for each frame, shown by 906, from the precision stage correlation magnitude (corr_ps) and predetermined threshold values limit_low and limit_high according to:

$$w = (corr\_ps - limit\_low)/(limit\_high - limit\_low)$$

If w>1, w=1
If w<0, w=0.
Therefore, w is a value between 0 and 1 and is calculated for every frame, and weighting transition range (from 0 to 1) is controlled by limit_low and limit_high. The displacement, strain and correlation sets of the robustness (902) and precision (904) stages are combined using the weighting value from 906, shown by box 908. The combination is done according to:

$$x = w * x\_ps + (1-w) * x\_rs$$

$$y = w * y\_ps + (1-w) * y\_rs$$

$$Sx = w*Sx\_ps + (1-w)*Sx\_rs$$

$$Sy = w*Sy\_ps + (1-w)*Sy\_rs$$

$$corr = w*corr\_ps + (1-w)*corr\_rs.$$

The combined displacement, strain and correlation sets are shown by box 910.

Figure 17:
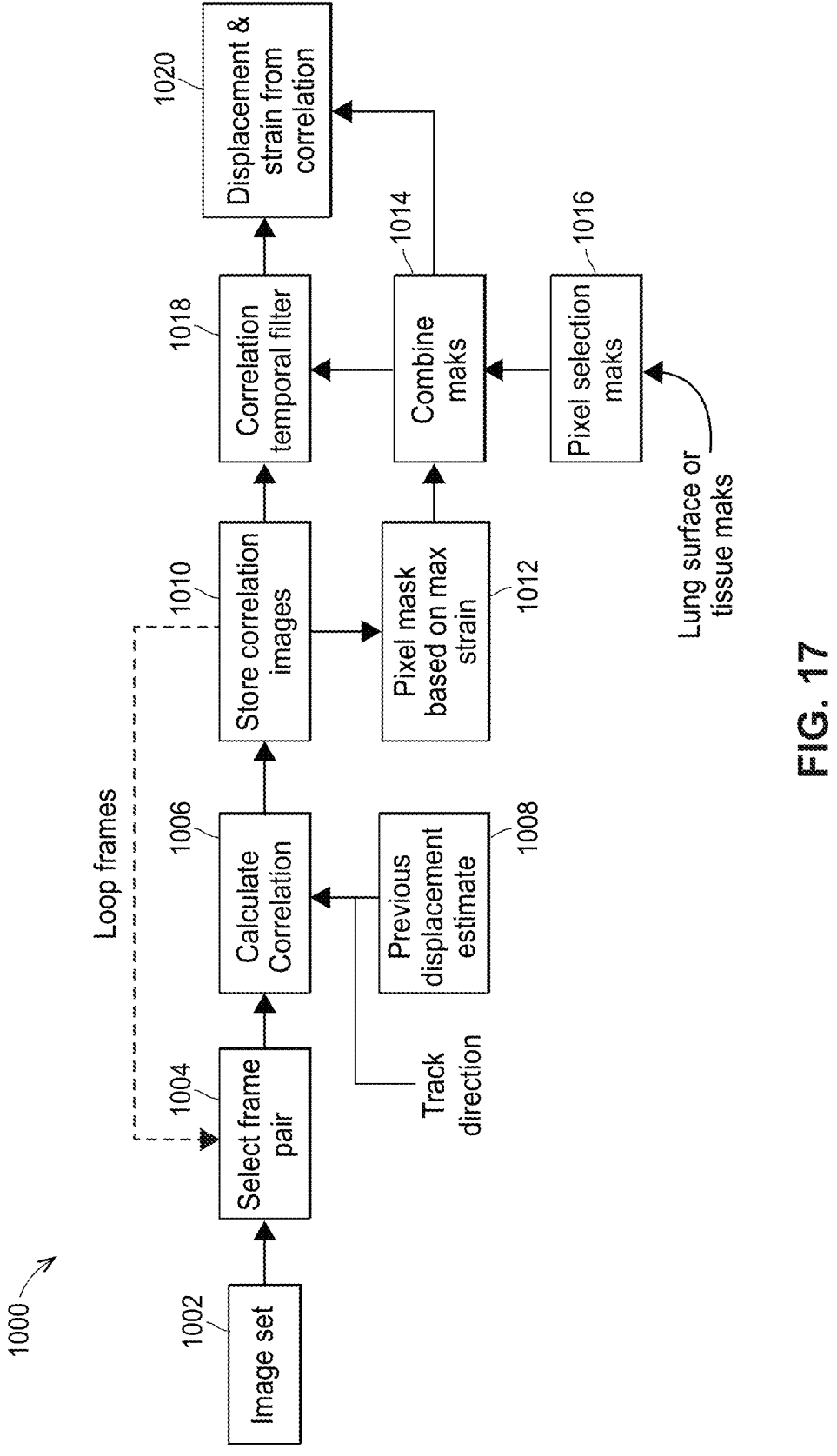
FIG. 17 illustrates a method of calculating displacement and strain, in accordance with an example.

FIG. 17 illustrates a method 1000 for calculating displacement and strain which is shown as box 810 in FIG. 15. At box 1002, an image set is provided, which is also shown as box 804 of FIG. 15. At box 1004, a pair of frames within the image set is selected. At box 1006, correlation between the pair of frames is calculated using a correlation method described in greater detail in FIG. 18. The correlation method incorporates a previous displacement estimate, shown at box 1008 and box 812 of FIG. 15. At box 1010, correlation images resulting from the correlation calculation are stored. Boxes 1004 to 1010 are iterative, meaning that after the correlation images are stored at box 1010, a new frame pair is selected from the correlation images at box 1004, correlation is calculated again, and a subsequent set of correlation images are stored. At box 1012, a pixel mask based on maximum strain is applied to the stored correlation images, which is described in greater detail in FIG. 19 below. At box 1014, the pixel mask based on maximum strain is combined with a pixel selection mask, shown at box 1016. The pixel selection mask is either the lung surface mask or tissue mask, dependent on which tracking path is being executed (lung tracking or tissue tracking), as described by FIG. 14. The combination of the masks is done by multiplying the pixels of each mask. The 'pixel selection mask' and 'pixel mask based on maximum strain' have values between 0 and 1 for each pixel of the image set. At box 1018, a correlation temporal filter is applied to the stored correlation images, shown at box 1010. The temporal filter may be a finite impulse response filter (FIR), or an infinite impulse response filter (IIR) or any other suitable filter. The filter operates across frames (time) for each pixel of the correlation images. At box 1020, displacement and strain are calculated from the correlation images that underwent the correlation temporal filter shown at box 1018 and combined masks shown at box 1014 in a method discussed in greater detail in FIG. 20.

Figure 19:
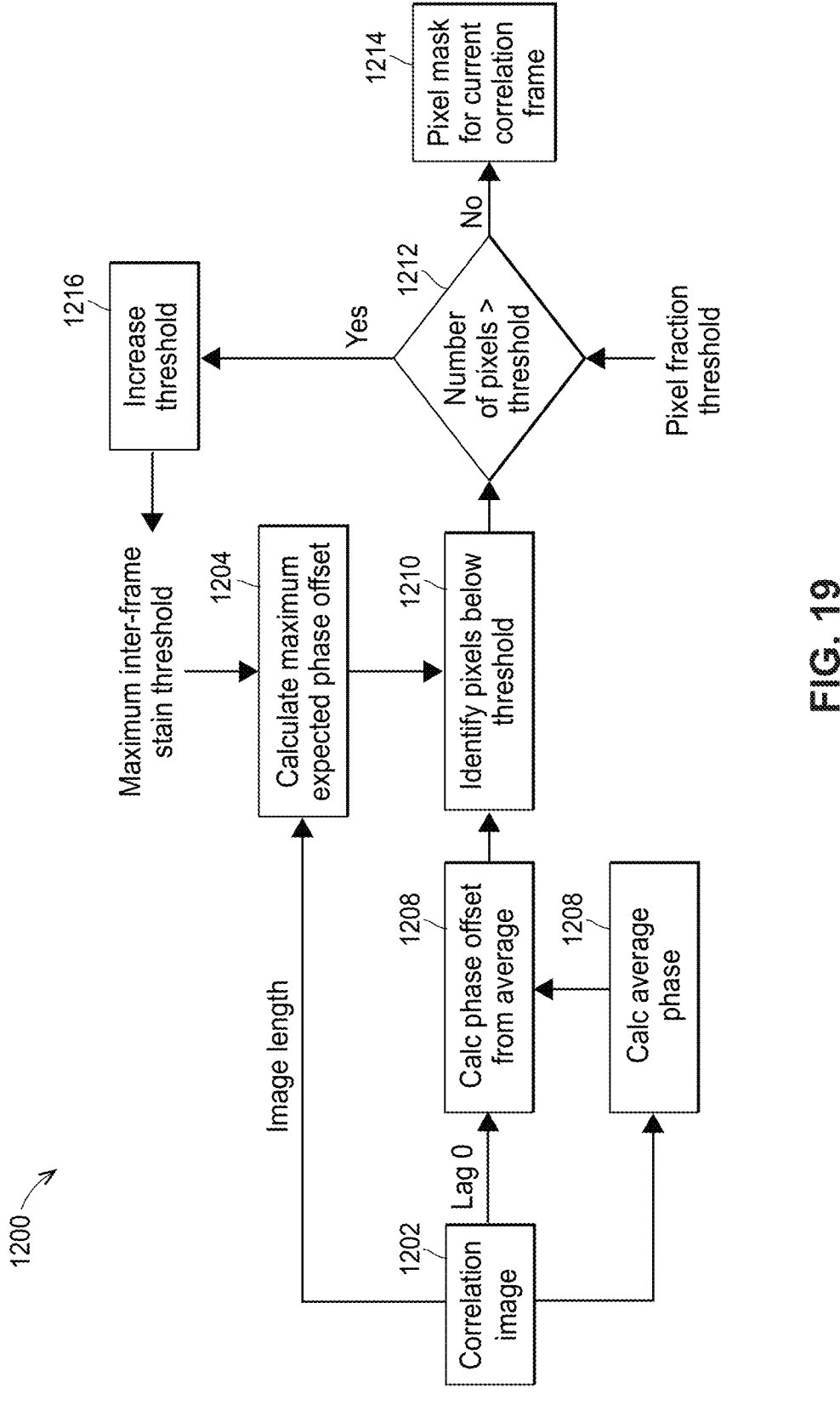
FIG. 19 illustrates a method of applying a pixel mask based on strain in conjunction with the method of FIG. 17, in accordance with an example.

Alternatively, the method of FIG. 17 could be done without a pixel selection mask (i.e., all pixels used for calculations) or without pixel mask based on max strain (i.e., no pixels are eliminated based on motion characteristics per FIG. 19 and proceeding description).

Figure 18:
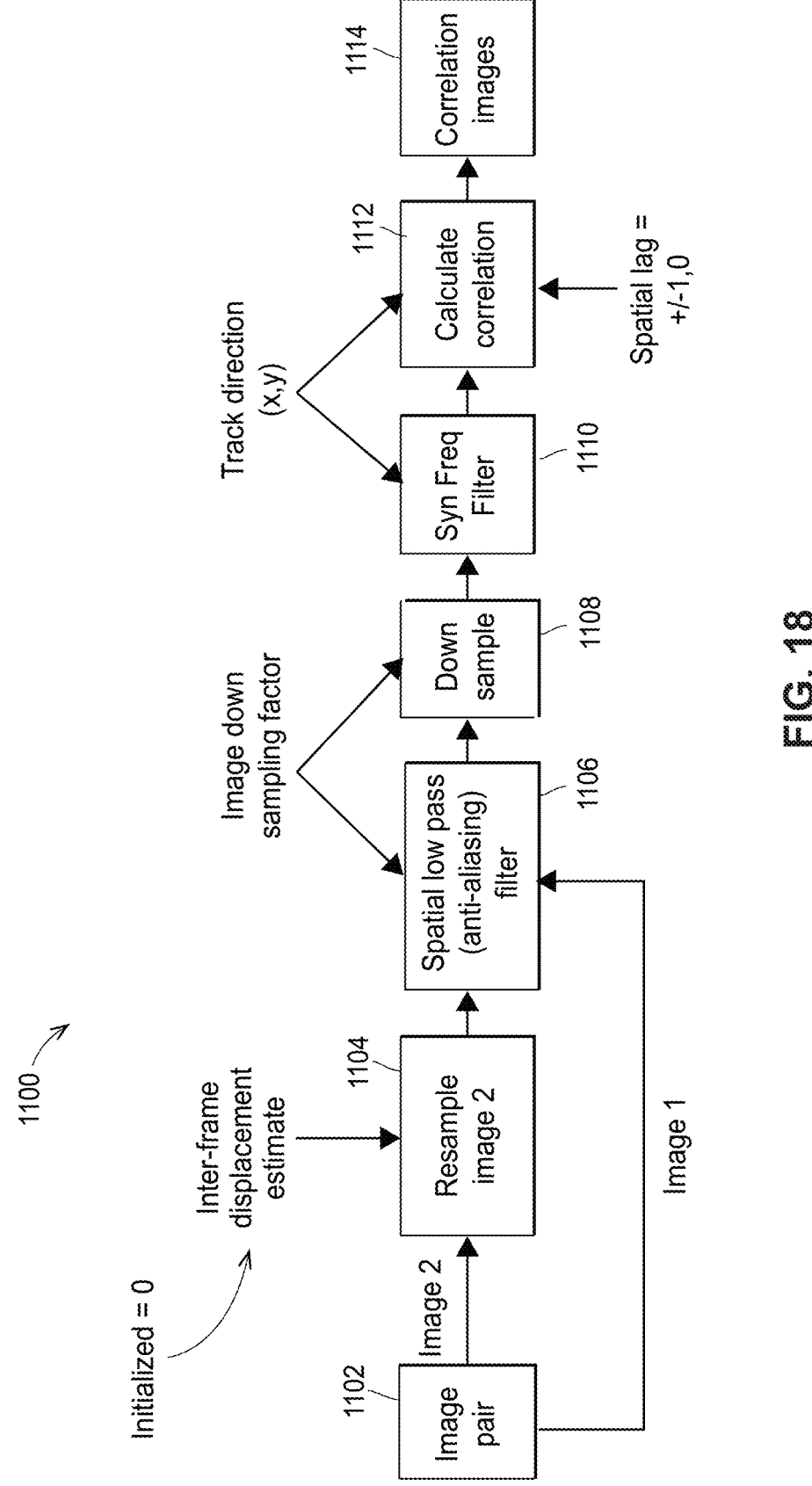
FIG. 18 illustrates a method of calculating correlation utilized in conjunction with the method of FIG. 17, in accordance with an example.

FIG. 18 illustrates a method 1100 of calculating correlation between a pair of frames of an image set, introduced at box 1006 of FIG. 17. At box 1102, a pair of images, from image set 1002 in FIG. 17, such as the pair of images selected at box 1004 of FIG. 17, is selected. At box 1104, an inter-frame displacement estimate is applied to one of the images of the pair (identified as "image 2"), which is subsequently known as "resampled image 2". The inter-frame displacement estimate is a single frame displacement estimate shown previously by 1008 from FIG. 17. As described previously, the interframe displacement estimate is calculated from tracking using the preceding down sampling value. This applies to tracking stages that are parameterized by multi-value down sampling, like the lung tracking precision stage described previously as part of FIG. 14. In the embodiment described by FIG. 14, the down sampling of 6 followed by down sampling of 3 is used for the lung tracking precision stage. Therefore the displacement estimates from the down sampling=6 tracking are used to resample image 2 per box 1104 of FIG. 18 when executing the down sampling=3 loop of FIG. 15. This multi-value down sampling provides a combination of large tracking range (i.e., the maximum interframe displacement that can be measured) and high precision since the tracking range is determined by the phase/pixel described by equation 7. With larger down sampling, the effective synthetic phase frequency reduces. For the first down sampling stage or for tracking stages that have only single value down sampling like tissue tracking or lung tracking robustness stage shown in FIG. 14, the inter-frame displacement value is set to zero (i.e., no resampling is done). At box 1106, a spatial low pass (anti-aliasing) filter is applied to the resample image 2 from box 1104 and to the other of the images of the pair (identified as "image 1"). The spatial low pass filter is a Hanning window FIR filter of length=(2*down sampling factor−1) pixels. The filtering is done both in x and y directions. The low pass filter could be other kind of FIR filter (e.g., box car, Gaussian, Kaiser), IIR filter or any suitable filter. Down sampling factor is the current down sampling used for tracking, determined by the down sampling set for the tracking stage being executed (tissue tracking, lung tracking precision stage, lung tracking robustness stage). Down sample, box 1108, is pixel decimation set by the down sampling (image down sampling factor). For example, every third pixel is selected (e.g., pixel number 1,4,7, . . . in both x & y, assuming monotonic pixel numbering indicating location of pixel in image) for down sample=3 to form a new image with fewer pixels and reduced spatial sampling frequency. A synthetic frequency filter is applied to the down sampled images (pair) at box 1110. The filter is a 1-D, complex, FIR filter described previously by FIG. 6. It is also called a synthetic phase filter. The filter is applied only along the track direction, as set by the loop presented in FIG. 15. The correlation images for spatial lags=+1, 0, −1 are calculated for the processed image pair, as shown in box 112. The spatial lag is done in the track direction (e.g., lag=1 corresponds to lag=1 in x direction for track direction=x). The correlation images are calculated according to equations 4 and 6 described previously. In this case, the covariance values described by the equations are normalized by the square root of the product of the signal power:

$$\rho(0) = \sigma(0) \Big/ \sqrt{\sum_x s_2(x)^2 \sum_x s_1(x)^2}$$

$$\rho(l) = \sigma(l) \Big/ \sqrt{\sum_x s_2(x)^2 \sum_x s_1(x-l)^2}$$

where $\rho$ is the correlation and l is lag. The normalization produces complex correlation values with magnitude between 0 and 1. The image spatial position vector is x (e.g., x,y pixel position) and the sum is done over the correlation window (e.g., a N×N pixel region). In this embodiment, at box 1114, the correlation and lag images are calculated for every pixel in the processed image pair. Alternatively, the processing illustrated by FIG. 18 could be done without downsampling or spatial low pass filtering. Resampling 1104 could be done after down sample 1108.

FIG. 19 illustrates a method 1200 of applying a pixel mask based on strain, such as the pixel mask discussed at box 1012 in FIG. 17. At box 1202, a correlation image (such as one of the correlation images stored at box 1010 of FIG. 17) is provided. The length of the correlation image is determined and, at box 1204, used in conjunction with a maximum inter-frame strain threshold to calculate a maximum expected phase offset. In addition, the correlation image is used to calculate an average phase at box 1206, which in combination with a zero lag covariance of the correlation image, is used to calculate a phase offset from average at box 1208. From the maximum expected phase offset calculated at box 1204 and the phase offset from average calculated at box 1208, pixels below a threshold are identified at box 1210. At box 1212, if the number of pixels is not greater than the threshold, the pixel mask for the current correlation frame is completed at box 1214. If the number of pixels is greater than the threshold, the threshold is increased at box 1216 and the new maximum inter-frame strain threshold is applied at box 1204 when calculating the maximum expected phase offset. The acts identified at steps 1216, 1204, and 1210 are repeated until the number of pixels exceeds the threshold.

Figure 20:
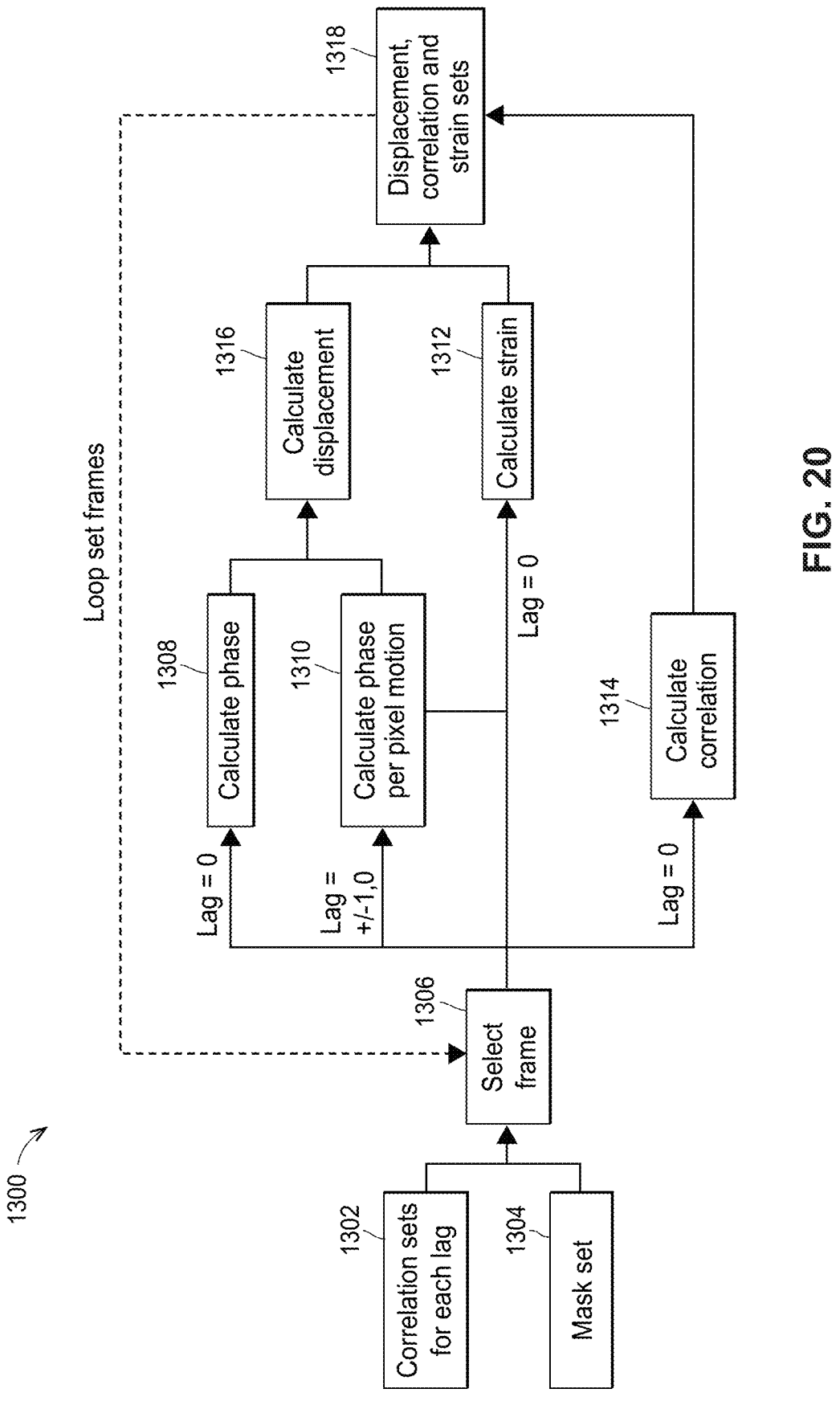
FIG. 20 illustrates a method of calculating displacement and strain from correlation utilized in conjunction with the method of FIG. 17, in accordance with an example.

FIG. 20 illustrates a method 1300 of calculating displacement and strain from correlation, such as the calculation discussed at box 1020 of FIG. 17. At box 1302, the correlation images that underwent a correlation temporal filter (such as those described at box 1018 of FIG. 17) are provided. At box 1304, the combined masks (such as those described at box 1014 of FIG. 17) are provided. From these two sets of images, a frame is selected at box 1306. From the correlation frame, the phase angle of the weighted spatial average of lag=0 correlation image is calculated at box 1308. The weighting for each pixel is determined by the mask frame. The weighted spatial average of the lag=1 and lag=−1 correlation images is calculated at box 1310. Additionally, the phase angle per pixel is calculated according to:

$$\text{angle}(\bar{\rho}(\pm 1)\bar{\rho}*(0)) = 2\pi f,$$

where $\bar{\rho}(0)$ is the weighted spatial average of lag=0 image and $\bar{\rho}(\pm 1)$ is the weighted spatial average of lag=1 or lag=−1 image, selected by the sign of $\bar{\rho}(0)$ by:

$$\bar{\rho}(\pm 1) = \bar{\rho}(1) \text{ if angle}(\bar{\rho}(0)) \geq 0$$

$$\bar{\rho}(\pm 1) = \bar{\rho}(-1) \text{ if angle}(\bar{\rho}(0)) < 0.$$

The displacement for the selected frame is calculated at box 1316 according to equation:

$$U = \frac{\text{angle}(\bar{\rho}(0))}{2\pi f}$$

where the numerator is the output of box 1308, the angle of the weighted spatial average of the lag=0 correlation image.

The strain is calculated at box 1312 in a method described in greater detail below. The correlation is calculated at box 1314, and is the magnitude of the weighted spatial average of the lag=0 correlation image given by the equation:

$$\text{Corr} = \text{mag}(\bar{\rho}*(0)).$$

Displacement and strain measurements described here and below measure lung surface and tissue motion and deformation (i.e., expansion and contraction). The correlation measurement produced at box 1314 also provides utility. The correlation coefficients (cc) are useful metrics for the assessing the quality of the strain and displacement estimates. Both very high and very low ccs can be indicators of disease and/or technical issues. High lung surface ccs imply lack of speckle variation consistent with low lung surface motion or gas in the pleural space representing a pneumothorax. Very low cc's strongly suggest that the tracking is poor, and any results need to be viewed with suspicion.

The displacement and strain are then identified as displacement, correlation and strain sets at box 1318, which may be looped back to select a new frame at box 1306 such that the process repeats iteratively.

Figure 21:
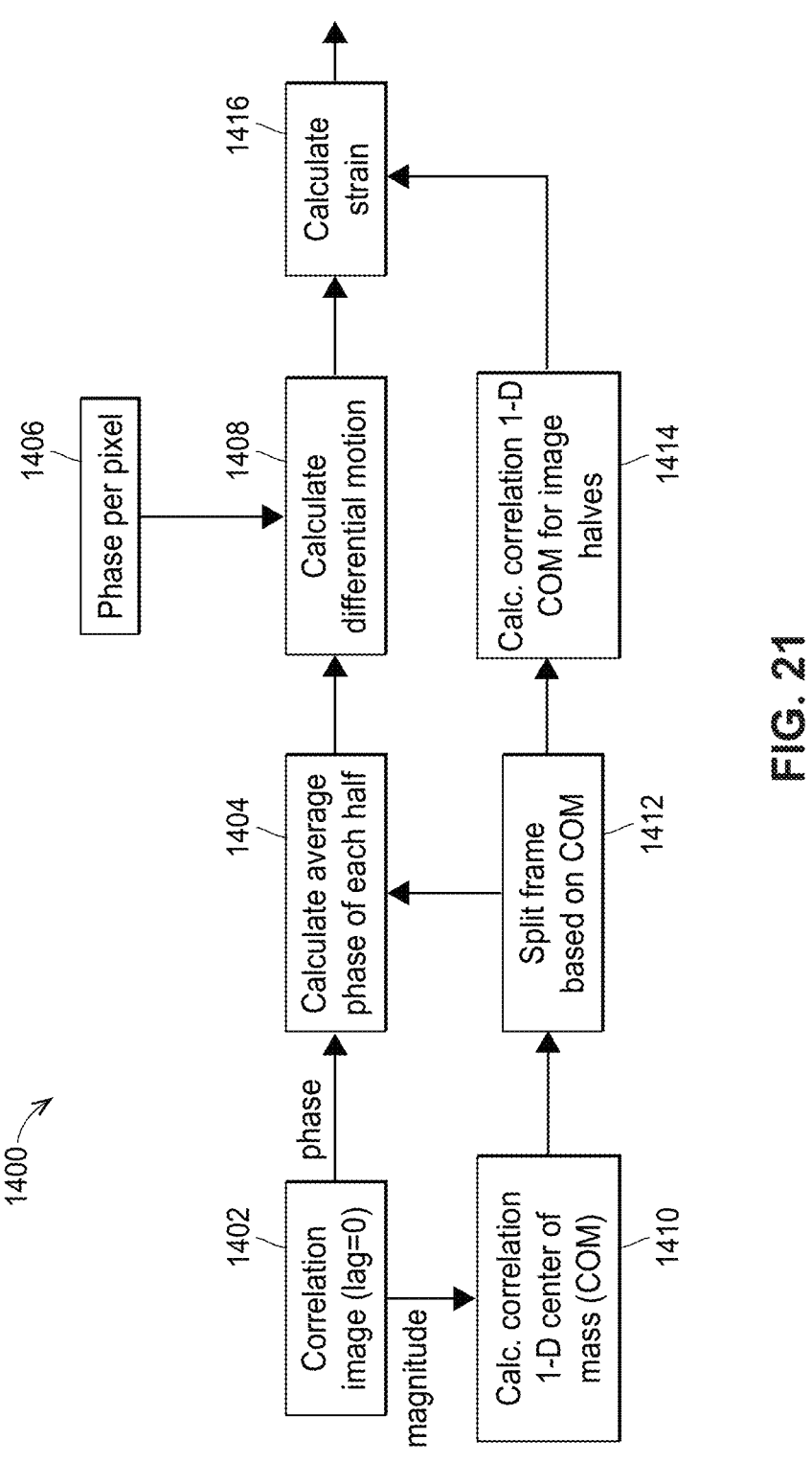
FIG. 21 illustrates a method of calculating lung surface strain, in accordance with an example.

FIG. 21 illustrates a method 1400 of calculating strain, such as the strain calculation performed at 1312 in FIG. 20. At box 1402, a correlation image is provided. At box 1404, an average phase of each half image is calculated. Similar to phase calculation of box 1308, the phase angle of the weighted spatial average of the lag=0 correlation image over each image half is performed. From that and a phase per pixel shown at box 1406, calculated according to the description of box 1310, differential motion is calculated at box 1408. The differential motion is calculated by subtracting the displacement measurements for each image half. The displacement of each image half is calculated according to:

$$U_{R,L} = \frac{\text{angle}(\bar{\rho}_{R,L}(0))}{2\pi f}$$

$$\Delta U = U_L - U_R$$

where R and L denote right and left image halves, respectively and AU is differential displacement. For example, angle($\bar{\rho}_R(0)$) is the phase angle of the weighted average of the lag=0 correlation image, calculated over the right half of the image.

Alternatively, the differential motion can be determined by calculating the weighted spatial average of the lag=0 correlation image for the right and left image halves, complex conjugate multiplying the average correlation for each half, calculating the phase angle of the complex conjugate multiply result, and dividing by the phase per pixel:

$$\Delta U = \frac{\text{angle}(\bar{\rho}(0)\bar{\rho}_R^*(0))}{2\pi f}$$

Meanwhile, at box 1410, the correlation 1-D center of mass (COM) is calculated. That is, the weighted average pixel coordinate is calculated, with correlation magnitude of the lag=0 correlation image used as the pixel weighting. At box 1412, the frame is split at on COM location, which determines the right and left image halves. More specifically, since the image is split based on correlation center of mass, the right and left images halves are technically the right and left image regions defined from the COM. At box 1414, the correlation 1-D COM for each image half is calculated. At box 1416, strain is calculated according to:

$$S = \Delta U / (\text{COM\_}L - \text{COM\_}R)$$

where COM_L and COM_R are the correlation center of mass locations for the left and right image halves, respectively.

Throughout this specification, plural instances may implement components, operations, or structures described as a single instance. Although individual operations of one or more methods are illustrated and described as separate operations, one or more of the individual operations may be performed concurrently, and nothing requires that the operations be performed in the order illustrated. Structures and functionality presented as separate components in example configurations may be implemented as a combined structure or component. Similarly, structures and functionality presented as a single component may be implemented as separate components. These and other variations, modifications, additions, and improvements fall within the scope of the subject matter herein.

Additionally, certain embodiments are described herein as including logic or a number of routines, subroutines, applications, or instructions. These may constitute either software (e.g., code embodied on a machine-readable medium or in a transmission signal) or hardware. In hardware, the routines, etc., are tangible units capable of performing certain operations and may be configured or arranged in a certain manner. In example embodiments, one or more computer systems (e.g., a standalone, client or server computer system) or one or more hardware modules of a computer system (e.g., a processor or a group of processors) may be configured by software (e.g., an application or application portion) as a hardware module that operates to perform certain operations as described herein.

In various embodiments, a hardware module may be implemented mechanically or electronically. For example, a hardware module may comprise dedicated circuitry or logic that is permanently configured (e.g., as a special-purpose processor, such as a field programmable gate array (FPGA) or an application-specific integrated circuit (ASIC)) to perform certain operations. A hardware module may also comprise programmable logic or circuitry (e.g., as encompassed within a general-purpose processor or other programmable processor) that is temporarily configured by software to perform certain operations. It will be appreciated that the decision to implement a hardware module mechanically, in dedicated and permanently configured circuitry, or in temporarily configured circuitry (e.g., configured by software) may be driven by cost and time considerations.

Accordingly, the term "hardware module" should be understood to encompass a tangible entity, be that an entity that is physically constructed, permanently configured (e.g., hardwired), or temporarily configured (e.g., programmed) to operate in a certain manner or to perform certain operations described herein. Considering embodiments in which hardware modules are temporarily configured (e.g., programmed), each of the hardware modules need not be configured or instantiated at any one instance in time. For example, where the hardware modules comprise a general-purpose processor configured using software, the general-purpose processor may be configured as respective different hardware modules at different times. Software may accordingly configure a processor, for example, to constitute a particular hardware module at one instance of time and to constitute a different hardware module at a different instance of time.

Hardware modules can provide information to, and receive information from, other hardware modules. Accordingly, the described hardware modules may be regarded as being communicatively coupled. Where multiple of such hardware modules exist contemporaneously, communications may be achieved through signal transmission (e.g., over appropriate circuits and buses) that connects the hardware modules. In embodiments in which multiple hardware modules are configured or instantiated at different times, communications between such hardware modules may be achieved, for example, through the storage and retrieval of information in memory structures to which the multiple hardware modules have access. For example, one hardware module may perform an operation and store the output of that operation in a memory device to which it is communicatively coupled. A further hardware module may then, at a later time, access the memory device to retrieve and process the stored output. Hardware modules may also initiate communications with input or output devices, and can operate on a resource (e.g., a collection of information).

The various operations of the example methods described herein may be performed, at least partially, by one or more processors that are temporarily configured (e.g., by software) or permanently configured to perform the relevant operations. Whether temporarily or permanently configured, such processors may constitute processor-implemented modules that operate to perform one or more operations or functions. The modules referred to herein may, in some example embodiments, comprise processor-implemented modules.

Similarly, the methods or routines described herein may be at least partially processor-implemented. For example, at least some of the operations of a method may be performed by one or more processors or processor-implemented hardware modules. The performance of certain of the operations may be distributed among the one or more processors, not only residing within a single machine, but also deployed across a number of machines. In some example embodiments, the processor or processors may be located in a single location (e.g., within a home environment, an office environment or as a server farm), while in other embodiments the processors may be distributed across a number of locations.

The performance of certain of the operations may be distributed among the one or more processors, not only residing within a single machine, but also deployed across a number of machines. In some example embodiments, the one or more processors or processor-implemented modules may be located in a single geographic location (e.g., within a home environment, an office environment, or a server farm). In other example embodiments, the one or more processors or processor-implemented modules may be distributed across a number of geographic locations.

Unless specifically stated otherwise, discussions herein using words such as "processing," "computing," "calculating," "determining," "presenting," "displaying," or the like may refer to actions or processes of a machine (e.g., a computer) that manipulates or transforms data represented as physical (e.g., electronic, magnetic, or optical) quantities within one or more memories (e.g., volatile memory, nonvolatile memory, or a combination thereof), registers, or other machine components that receive, store, transmit, or display information.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

Some embodiments may be described using the expression "coupled" and "connected" along with their derivatives. For example, some embodiments may be described using the term "coupled" to indicate that two or more elements are in direct physical or electrical contact. The term "coupled," however, may also mean that two or more elements are not in direct contact with each other, but yet still co-operate or interact with each other. The embodiments are not limited in this context.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

In addition, use of the "a" or "an" are employed to describe elements and components of the embodiments herein. This is done merely for convenience and to give a general sense of the description. This description, and the claims that follow, should be read to include one or at least one and the singular also includes the plural unless it is obvious that it is meant otherwise.

While the present invention has been described with reference to specific examples, which are intended to be illustrative only and not to be limiting of the invention, it will be apparent to those of ordinary skill in the art that changes, additions and/or deletions may be made to the disclosed embodiments without departing from the spirit and scope of the invention.

The foregoing description is given for clearness of understanding; and no unnecessary limitations should be understood therefrom, as modifications within the scope of the invention may be apparent to those having ordinary skill in the art.

The following are lettered aspects of the invention:

Aspect A: A method of estimating lung motion, the method comprising:

collecting a time series of ultrasound images of a lung surface, the time series including a plurality of frames;

identifying a lung surface in one of the plurality of frames;

subsetting, by a processor, each of the plurality of frames into at least one sub-image to form a raw set of sub-images;

applying a tissue region mask to each sub-image in the raw set of sub-images to create a tissue region mask set of sub-images;

applying a temporal filter within a robustness stage to each sub-image in the raw set of sub-images to create a temporally filtered robustness set of sub-images;

applying a lung surface mask to each sub-image in the raw set of sub-images to create a lung surface mask set of sub-images;

applying a temporal filter within a precision stage to each sub-image in the raw set of sub-images to create a temporally filtered precision set of sub-images;

performing tissue tracking by tracking the raw set of sub-images and the tissue region mask set of sub-images to create tissue tracking data;

performing lung tracking by tracking the temporally-filtered robustness set of sub-images and the lung surface mask set of sub-images to create first lung tracking data, tracking the temporally filtered precision set of sub-images and the lung surface mask set of sub-images to create second lung tracking data, and combining the first lung tracking data and the second lung tracking data to create stage combination data;

quantifying displacement and strain based on the tissue tracking data and the stage combination data.

Aspect B: The method of aspect A, wherein tracking the raw set of sub-images and the tissue region mask set of sub-images to create tissue tracking data comprises selecting an image down sampling factor comprising a plurality of down sample values, selecting a track direction, and for each down sample value, calculating displacement, strain, and correlation in the track direction from the raw set of sub-images and the tissue region mask set of sub-images.

Aspect C: The method of aspect A, wherein tracking the temporally-filtered robustness set of sub-images and the lung surface mask set of sub-images to create first lung tracking data comprises iteratively selecting an image down sampling factor comprising a plurality of down sample values, selecting a track direction, and for each down sample value, calculating displacement, strain, and correlation in the track direction from the temporally-filtered robustness set of sub-images and the lung surface mask set of sub-images, wherein, after an initial iteration, calculating displacement and strain includes utilizing a previously calculated displacement, strain, or correlation associated with one of the plurality of down sample values.

Aspect D: The method of aspect A, wherein tracking the temporally filtered precision set of sub-images and the lung surface mask set of sub-images to create second lung tracking data comprises iteratively selecting an image down sampling factor comprising a plurality of down sample values, selecting a track direction, and for each down sample value, calculating displacement, strain, and correlation in the track direction from the temporally-filtered precision set of sub-images and the lung surface mask set of sub-images, wherein, after an initial iteration, calculating displacement and strain includes utilizing a previously calculated displacement, strain, or correlation associated with one of the plurality of down sample values.

Aspect E: The method of aspect A, wherein combining the first lung tracking data and the second lung tracking data to create stage combination data comprises providing a displacement, strain, and correlation set forming the first lung tracking data, the displacement, strain, and correlation set forming the first lung tracking data including a displacement value, a strain value, and a correlation value for each frame of the temporally-filtered robustness set of sub-images and the lung surface mask set of sub-images, providing a displacement, strain, and correlation set forming the second lung tracking data, the displacement, strain, and correlation set forming the second lung tracking data including a displacement value, a strain value, and a correlation value for each frame of the temporally-filtered precision set of sub-images and the lung surface mask set of sub-images, calculating a robustness weighting value for each frame of the temporally-filtered robustness set of sub-images and the lung surface mask set of sub-images from a robustness stage correlation magnitude and robustness predetermined threshold limits, calculating a precision weighting value for each frame of the temporally-filtered precision set of sub-images and the lung surface mask set of sub-images from a precision state correlation magnitude and precision predetermined threshold limits, and combining the first lung tracking data and the second lung tracking data using the robustness weighting value and the precision weighting value.

Aspect F: The method of aspect A, wherein quantifying displacement and strain based on the tissue tracking data and the stage combination data comprises

25

26 iteratively selecting a frame pair from the time series of ultrasound images of the lung surface, calculating correlation between the frame pair, and storing the resulting correlation images, wherein after an initial iteration, calculating correlation between the frame pair includes a previous displacement estimate in a track direction, applying a pixel mask based on maximum strain to the stored resulting correlation images, combining the pixel mask based on maximum strain with a pixel selection mask and applying the combined pixel mask and pixel selection mask to the stored resulting correlation images, applying a correlation temporal filter to the stored resulting correlation images, and calculating displacement and strain from the stored resulting correlation images that underwent the combined pixel mask and pixel selection mask and the correlation temporal filter.

Aspect G: The method of Aspect F, wherein calculating correlation comprises selecting a frame pair from the time series of ultrasound images of the lung surface, applying an inter-frame displacement estimate to one image of the frame pair to create a resample image, applying a spatial low-pass filter to the resample image, applying a down sample pixel decimation set to create a down sampled image pair, applying a synthetic frequency filter to the down sampled image pair, and calculating correlation for each pixel in the down sampled image pair.

Aspect H: The method of Aspect F, wherein applying a pixel mask based on max strain comprises providing a correlation image from the stored resulting correlation images, performing an iterative process comprising determining a length of the correlation image, using the length of the correlation image and a maximum inter-frame strain threshold to calculate a maximum expected phase offset, using the correlation image to calculate an average phase, using the average phase and a zero lag covariance of the correlation image to calculate a phase offset from average, from the maximum expected phase offset and the phase offset from average, identifying pixels below a threshold, when a total number of the pixels is less than or equal to the threshold, increasing the threshold and calculating a new maximum inter-frame strain threshold for use in subsequent iterations of the iterative process, and when a number of the pixels is not greater than the threshold, completing the pixel mask for the correlation image.

Aspect I: The method of Aspect F, wherein calculating displacement and strain from correlation comprises iteratively selecting a frame from the stored resulting correlation images that underwent the combined pixel mask and pixel selection mask and the correlation temporal filter, from the selected frame, calculating a phase angle of a weighted spatial average of a lag=0 correlation image, calculating a weighting for each pixel, calculating a weighted spatial average of a lag=1 correlation image and a lag=−1 correlation image, calculating a phase angle per pixel, calculating strain, calculating displacement, and calculating correlation that is the magnitude of the weighted spatial average of the lag=0 correlation image.

Aspect J: The method of aspect F, wherein calculating displacement and strain from correlation comprises iteratively selecting a frame from the stored resulting correlation images that underwent the combined pixel mask and pixel selection mask and the correlation temporal filter, from the selected frame, calculating a phase angle of a weighted spatial average of a lag=0 correlation image, calculating a weighting for each pixel, calculating a weighted spatial average of a lag=1 correlation image and a lag=−1 correlation image, calculating a phase angle per pixel, calculating strain, calculating displacement, and calculating correlation that is the magnitude of the weighted spatial average of the lag=0 correlation image.

Aspect K: The method of Aspect J, wherein calculating strain comprises from the selected frame, calculating an average phase of each half image, calculating differential motion from a phase angle of a weighted spatial average of a lag=0 correlation image of each half image and the phase angle per pixel, calculating the correlation 1-D center of mass, splitting the selected frame at the correlation 1-D center of mass into a right image half and a left image half, calculating a 1-D center of mass for the right image half and calculating a 1-D center of mass for the left image half, and calculating strain from the 1-D center of mass for the right image half and the 1-D center of mass for the left image half.

What is claimed:

1. A method of estimating lung motion, the method comprising:

collecting a time series of B-mode ultrasound images of a lung surface, the time series including a plurality of frames;

identifying a lung surface in one of the plurality of frames;

subsetting, by a processor, each of the plurality of frames into at least one sub-image with the lung surface arranged along the x-axis of the at least one sub-image;

applying a spatial filter along an x-axis of each sub-image to transform each pixel of each sub-image into ultrasound B-mode data, the ultrasound B-mode data including a real component and an imaginary component, the ultrasound B-mode data compiled in a complex data set, each complex data set associated with one of the plurality of frames, and calculating inter-frame motion data of a window location from the complex data sets associated respectively with a first frame of the plurality of frames and a second frame of the plurality of frames that is temporally successive to the first frame of the plurality of frames, wherein the ultrasound B-mode data is pulse-range data represented by $s(x)=A(x-U)e^{-i2\pi f(x-U)}$, where x is a digital spatial coordinate of a pixel, U is a position of a signal, A(x–U) is a signal amplitude profile, and f is a spatial center frequency of a complex signal, and wherein a phase of s(x), the pulse-range data, is proportional to a difference of x, the digital spatial coordinate of the pixel, and U, the position of the signal.

2. The method of claim 1, wherein identifying a lung surface in one of the plurality of frames comprises drawing a line between a right edge and a left edge of the lung surface in one of the plurality of frames.

3. The method of claim 2, wherein the line is drawn by an operator using software on a computer.

4. The method of claim 2, wherein subsetting each of the plurality of frames into at least one sub-image is based on a location of the line.

5. The method of claim 4, wherein subsetting each of the plurality of frames of the time series includes, for the one of the plurality of frames on which the line is drawn, identifying a sub-image having a fixed number of pixels above the line and below the line, and for remaining frames of the plurality of frames, identifying a sub-image for each of the remaining frames having a same set of pixels as the sub-image of the one of the plurality of frames on which the line is drawn.

6. The method of claim 1, wherein identifying a lung surface in one of the plurality of frames and subsetting each of the plurality of frames into at least one sub-image is automated by use of image segmentation algorithms.

7. The method of claim 1, wherein the spatial filter is a synthetic phase filter or a gradient filter.

8. The method of claim 1, further comprising applying a spatial filter along a y-axis of each sub-image.

9. The method of claim 1, wherein calculating inter-frame motion data comprises extracting a first signal from a correlation window of the first frame and a second signal from the correlation window of the second frame, the correlation window being a same location in the first frame and the second frame, where the first signal is represented by $s_1(x)=A_1(x-U_1)e^{-i2\pi f(x-U_1)}$ and the second signal is represented by $s_2(x)=A_2(x-U_2)e^{-i2\pi f(x-U_2)}$.

10. The method of claim 9, wherein calculating inter-frame motion data further comprises calculating a sum of a complex conjugate multiple of the first signal and the second signal, which is a zero lag covariance of $s_1$ and $s_2$ and is represented by $$\sigma(0) = \sum_x s_2(x)*s_1^*(x) = \sum_x A_2(x-U_2)e^{-i2\pi f(x-U_2)}A_1(x-U_1)e^{i2\pi f(x-U_1)}$$

11. The method of claim 10, wherein calculating inter-frame motion data further comprises calculating a phase angle of the zero lag covariance of $s_1$ and $s_2$, which is a phase angle of the sum of the complex conjugate multiple of the first signal and the second signal, represented by $$\text{angle } (\sigma(0)) = \text{angle } (s_2(x)s_1^*(x)) = 2\pi f(U_2-U_1).$$

12. The method of claim 10, wherein calculating inter-frame motion data further comprises calculating a lag 1 covariance, which is the complex conjuate multiple with $s_1$ shifted by one pixel, represented by $$\sigma(1) = \sum_x s_2(x-1)s_1^*(x) = \sum_x A_2(x-1-U_2)e^{-i2\pi f(x-U_2-1)}A_1(x-U_1)e^{i2\pi f(x-U_1)}.$$

13. The method of claim 12, wherein calculating inter-frame motion data further comprises calculating a phase angle of a complex conjugate multiple of the zero lag covariance and the lag 1 covariance as represented by angle($\sigma(1)\sigma(0)$)=2$\rho$f.

14. The method of claim 13, wherein calculating inter-frame motion data further comprises calculating a displacement represented by $\Delta U_{1,2}=2\pi f(U_2-U_1)/2\pi f$.

15. The method of claim 14, further comprising identifying pairs of the plurality of frames, each frame having a temporally successive frame and identified as forming a pair that includes the frame and the temporally successive frame, and calculating inter-frame motion for all pairs of the plurality of frames from the complex data sets associated with the frame and the temporally successive frame of each pair, and wherein the displacement is calculated for each window location of each sub-image for all pairs of the plurality of frames.

16. The method of claim 1, further comprising identifying pairs of the plurality of frames, each frame having a temporally successive frame and identified as forming a pair that includes the frame and the temporally successive frame, and calculating inter-frame motion for all pairs of the plurality of frames from the complex data sets associated with the frame and the temporally successive frame of each pair.

17. The method of claim 1, wherein a segmentation algorithm is applied to identify pixels from the lung surface, and wherein lung surface motion is calculated from displacement of pixels identified as the lung surface.

18. The method of claim 1, further comprising applying a high pass temporal filter, a band pass filter, or an all pass filter to each sub-image.

* * * * *